US012472305B2

(12) United States Patent
Yeh

(10) Patent No.: US 12,472,305 B2
(45) Date of Patent: Nov. 18, 2025

(54) SYRINGE

(71) Applicant: CC BIOTECHNOLOGY CORPORATION, Tainan (TW)

(72) Inventor: Chin-Min Yeh, Tainan (TW)

(73) Assignee: CC BIOTECHNOLOGY CORPORATION, Tainan (TW)

( * ) Notice: Subject to any disclaimer, the term of this patent is extended or adjusted under 35 U.S.C. 154(b) by 635 days.

(21) Appl. No.: 17/920,901

(22) PCT Filed: Apr. 28, 2020

(86) PCT No.: PCT/CN2020/087378
§ 371 (c)(1),
(2) Date: Oct. 24, 2022

(87) PCT Pub. No.: WO2021/217390
PCT Pub. Date: Nov. 4, 2021

(65) Prior Publication Data
US 2023/0181831 A1 Jun. 15, 2023

(51) Int. Cl.
*A61M 5/24* (2006.01)
*A61M 5/315* (2006.01)

(52) U.S. Cl.
CPC ...... *A61M 5/2422* (2013.01); *A61M 5/31548* (2013.01); *A61M 2005/2403* (2013.01)

(58) Field of Classification Search
CPC ............ A61M 5/2422; A61M 5/31548; A61M 2005/2403
See application file for complete search history.

(56) References Cited

U.S. PATENT DOCUMENTS 5,084,017 A 1/1992 Maffetone
5,938,642 A 8/1999 Burroughs et al.
7,291,132 B2 11/2007 DeRuntz et al.
7,427,275 B2 9/2008 DeRuntz et al.
7,918,833 B2 4/2011 Veasey et al.
9,005,160 B2 4/2015 Karlsson et al.
9,072,838 B2 7/2015 Hogdahl
(Continued)

FOREIGN PATENT DOCUMENTS

CN 1835774 A 9/2006
CN 101829381 A 9/2010
(Continued)

*Primary Examiner* — Dung T Ulsh
(74) *Attorney, Agent, or Firm* — Best & Flanagan LLP

(57) ABSTRACT

A syringe has an injection mechanism configured to be detachably connected to a medicine vial. The injection mechanism can be manually triggered to convert an injection mode and a standby mode; the injection mechanism has a housing, a spiral pushing assembly, a metering guide sleeve, a total volume control nut, a diagonal tension knob, and a metering screw; after the medicament liquid in the medicine vial is used up, a user can remove the medicine vial, the injection mechanism can be converted into the standby mode, and non-return ratchet buckles of the metering guide sleeve can be disengaged from a one-way ratchet portion of the housing; thus, the metering screw can be pushed back to an original position, and the total volume control nut is pushed back to an initial full volume position of the metering guide sleeve, so that the syringe can be reused.

20 Claims, 18 Drawing Sheets

(56) References Cited

U.S. PATENT DOCUMENTS

| | | | | |
|---|---|---|---|---|
| 9,186,459 | B2 * | 11/2015 | Bechmann | A61M 5/3204 |
| 9,205,195 | B2 * | 12/2015 | Burren | A61M 5/31556 |
| 9,345,838 | B2 | 5/2016 | Plumptre et al. | |
| 9,764,091 | B2 | 9/2017 | Bechmann et al. | |
| 9,775,948 | B2 | 10/2017 | Bechmann et al. | |
| 10,220,152 | B2 * | 3/2019 | Cammish | A61M 5/31595 |
| 10,293,112 | B2 | 5/2019 | Plumptre et al. | |
| 10,350,359 | B2 | 7/2019 | Burren et al. | |
| 10,576,210 | B2 * | 3/2020 | Plumptre | A61M 5/31551 |
| 10,702,659 | B2 | 7/2020 | Morris et al. | |
| 10,869,968 | B2 | 12/2020 | Meier | |
| 10,933,201 | B2 | 3/2021 | Lam | |
| 11,426,524 | B2 | 8/2022 | Burren et al. | |
| 11,813,438 | B2 | 11/2023 | Plumptre | |
| 12,023,472 | B2 | 7/2024 | Burren et al. | |
| 12,194,279 | B2 | 1/2025 | Hacker et al. | |
| 2006/0206057 | A1 | 9/2006 | DeRuntz et al. | |
| 2013/0131605 | A1 | 5/2013 | Hiles | |
| 2014/0364766 | A1 | 12/2014 | Devgon et al. | |
| 2019/0060576 | A1 | 2/2019 | Kwolek et al. | |
| 2020/0405958 | A1 | 12/2020 | Hacker et al. | |
| 2022/0047817 | A1 | 2/2022 | Hostettler et al. | |
| 2024/0058544 | A1 | 2/2024 | Ni et al. | |
| 2024/0082493 | A1 | 3/2024 | Nimkar et al. | |

FOREIGN PATENT DOCUMENTS

| | | | |
|---|---|---|---|
| CN | 102665802 | A | 9/2012 |
| CN | 102716529 | A | 10/2012 |
| CN | 203090111 | U | 7/2013 |
| CN | 103547304 | A | 1/2014 |
| CN | 103945879 | A | 7/2014 |
| CN | 103945879 | B | 8/2017 |
| CN | 208905879 | U | 5/2019 |
| CN | 110382021 | A | 10/2019 |
| EP | 0937471 | A2 | 8/1999 |
| EP | 2379138 | A1 | 10/2011 |
| EP | 2452711 | A1 | 5/2012 |
| EP | 2083890 | B1 | 12/2018 |
| EP | 3412323 | A1 | 12/2018 |
| EP | 3247429 | B1 | 6/2019 |
| EP | 2890434 | B1 | 4/2020 |
| EP | 2983741 | B1 | 6/2020 |
| EP | 3041546 | B1 | 1/2021 |
| EP | 3256195 | B1 | 9/2021 |
| EP | 3895747 | A1 | 10/2021 |
| EP | 3669913 | B1 | 11/2024 |
| JP | 2005508205 | A | 3/2005 |
| JP | 2007502146 | A | 2/2007 |
| JP | 2016514605 | A | 5/2016 |
| JP | 2017510333 | A | 4/2017 |
| JP | 6546153 | B2 | 7/2019 |
| JP | 6637974 | B2 | 1/2020 |
| TW | M483803 | U | 8/2014 |
| TW | 202010528 | A | 3/2020 |
| WO | 2020047841 | A1 | 3/2020 |

* cited by examiner

SYRINGE

CROSS-REFERENCE TO RELATED INVENTIONS

This invention patent application is a national stage entry under 35 U.S.C. 371 and claims the benefit of International Invention Application No. PCT/CN2020/087378, filed on Apr. 28, 2020. The entire contents of which are hereby incorporated herein by reference thereto.

BACKGROUND OF THE INVENTION

Field of the Invention

The present invention relates to a syringe, and especially to a syringe that can be assembled with a medicine vial to perform quantitative output of medicament liquid for multiple times, and can be replaced with another full medicine vial for reuse after medicament liquid in the medicine vial is completely used up.

Description of Related Art

Based on the safety regulations for medicament liquid injection, a conventional syringe already has a function of being repeatedly used for a limited times. The conventional syringes are distinguished into a type of dose metering syringes and a type of frequency metering syringes. Regarding a conventional dose metering syringe, after the dose metering syringe is connected to a medicine vial, a pushing rod disposed at a rear end of the syringe is pushed, and a piston in the medicine vial is pushed to move for a predetermined distance via an interaction of a pushing mechanism mounted therein, thereby outputting a predetermined dose of medicament liquid through a needle connected to a front end of the medicine vial.

The conventional dose metering syringe is capable of achieving the function of outputting a predetermined dose of medicament liquid or further has a function of labor-saving in manipulation. However, after the medicament liquid in the medicine vial connected to the conventional dose metering syringe is used up, because the pushing mechanism in the syringe does not have a function to return to an original condition, all the conventional syringes need to be discarded and cannot be reused.

SUMMARY OF THE INVENTION

The technical problem to be solved by the present invention is: to provide a syringe to solve the problem that the conventional dose metering syringe cannot restore an original condition to be reused after being used.

The technical solution proposed by the present invention is: to provide a syringe detachably assembled with a medicine vial containing medicament liquid and a needle component connected to a front end of the medicine vial. Wherein the syringe defines a central axis extending along a front-to-rear direction of the syringe; the syringe comprises an injection mechanism. The injection mechanism has an injection mode and a standby mode, and is able to be manually triggered to perform a conversion between the injection mode and the standby mode. The injection mechanism comprises:

a housing having a movable space formed through the housing along the central axis, a front end of the housing detachably connected to the medicine vial; and a one-way ratchet portion formed on a peripheral wall of the movable space at a front segment of the movable space of the housing;

a spiral pushing assembly mounted in the movable space of the housing and being capable of spirally moving around the central axis; the spiral pushing assembly extending to an outside of a rear end of the housing; and the spiral pushing assembly being able to be pushed to generate a spiral propulsion;

a metering guide sleeve mounted in the housing, being capable of rotating at a fixing point; and the metering guide sleeve inserted into the spiral pushing assembly and able to be controlled to connect and rotate with the spiral pushing assembly; the metering guide sleeve comprising a guide sleeve body and multiple non-return ratchet buckles; the guide sleeve body having a guide sleeve central hole, at least one spiral portion formed on an inner peripheral wall of the guide sleeve central hole; a guide sleeve threaded portion formed on a rear segment of an outer peripheral surface of the guide sleeve body; and a guide sleeve front end portion formed at a front end of the guide sleeve body; the multiple non-return ratchet buckles formed on an external surface of the guide sleeve front end portion; when the multiple non-return ratchet buckles controlled to engage with the one-way ratchet portion of the housing, the metering guide sleeve solely driven to rotate forwardly and in said injection mode; when the multiple non-return ratchet buckles disengaging from the one-way ratchet portion of the housing, the metering guide sleeve able to rotate forwardly or backwardly and in said standby mode;

a total volume control nut mounted in the spiral pushing assembly, being capable of linearly moving along the central axis, and screwed with the guide sleeve threaded portion at a rear segment of the metering guide sleeve;

a diagonal tension knob mounted in the front end of the housing and being movable along the central axis; the diagonal tension knob being drivable to change an engaging condition of the non-return ratchet buckles relative to the one-way ratchet portion of the housing and to convert the said injection mode and the said standby mode; and a metering screw inserted in the diagonal tension knob and the housing and the metering screw screwed within the metering guide sleeve; the metering screw having a screw body having a screw threaded portion and the metering screw screwed with said spiral portion inside the metering guide sleeve via the screw threaded portion; a front end of the metering screw extending in front of the diagonal tension knob; a spiral movement of the metering guide sleeve able to drive the metering screw to move linearly along the central axis inside the housing to perform a quantitative output of the medicament liquid in the medicine vial; when the injection mechanism in the standby mode, the metering screw being able to linearly move backward and be received into the housing along the central axis.

According to the above-mentioned syringe, the syringe comprises a cartridge sleeve. The cartridge sleeve has a containing space formed through and within the cartridge sleeve along the central axis. The cartridge sleeve is detachably installed to the medicine vial, and a front end of the cartridge sleeve is detachably installed to the needle component. The cartridge sleeve is able to be connected to the front end of the housing of the injection mechanism. The cartridge sleeve is able to trigger the diagonal tension knob to move backward and to drive the multiple non-return ratchet buckles to engage with the one-way ratchet portion of the housing and in the said injection mode. When the cartridge sleeve is detached from the front end of the housing of the injection mechanism, the diagonal tension knob is able to move forward to make the multiple non-return ratchet buckles disengage from the one-way ratchet portion of the housing and in the said standby mode.

According to the above-mentioned syringe, the cartridge sleeve comprises a cartridge body. The cartridge body has at least one viewing window formed in a peripheral wall of the cartridge body. A connection portion is formed at a rear end of the cartridge body. A positioning flange is formed on the peripheral wall of the cartridge body and located at a front end of the connection portion. Multiple engaging protrusions are formed on an outer peripheral surface of the connection portion. The front end of the housing is a cartridge sleeve connecting portion. Multiple L-shaped engaging grooves are formed in an inner peripheral wall of the cartridge sleeve connecting portion. Each L-shaped engaging groove includes a straight groove section being parallel to the central axis and a transverse section connected to a rear end of the straight groove section. When the connection portion at the rear end of the cartridge sleeve is inserted into the cartridge sleeve connecting portion at the front end of the housing, each engaging protrusion is able to slide along the straight groove section of a respective one of the L-shaped engaging grooves and to turn into an end of the transverse section of the respective one of the L-shaped engaging grooves to lock the cartridge sleeve to the front end of the housing.

According to the above-mentioned syringe, a guiding ring is formed in the front end of the housing. An outer peripheral surface of the guiding ring is connected to the peripheral wall of the movable space via multiple arms. A spacing is formed between the guiding ring and the peripheral wall of the movable space. At least one guiding block is formed on an inner annular wall of the guiding ring. The screw body of the metering screw has at least one axial guiding groove passing through the screw threaded portion and being parallel to the central axis. The axial guiding groove engages with the guiding block inside the guiding ring of the housing.

According to the above-mentioned syringe, each non-return ratchet buckle has a wing protruding forwardly and disposed at a front end face of the non-return ratchet buckle. The diagonal tension knob has a conical surface abutting against the wing of each non-return ratchet buckle to let the conical surface of the diagonal tension knob push the non-return ratchet buckle to engage with the one-way ratchet portion of the housing via the wing.

According to the above-mentioned syringe, the syringe comprises a cartridge sleeve. The cartridge sleeve has a containing space formed through and within the cartridge sleeve along the central axis. The cartridge sleeve is detachably installed to the medicine vial, and a front end of the cartridge sleeve is detachably installed to the needle component. The cartridge sleeve is able to be connected to the front end of the housing of the injection mechanism. The cartridge sleeve is able to trigger the diagonal tension knob to move backward and to drive the multiple non-return ratchet buckles to engage with the one-way ratchet portion of the housing and in the said injection mode. When the cartridge sleeve is detached from the front end of the housing of the injection mechanism, the diagonal tension knob is able to move forward to make the multiple non-return ratchet buckles disengage from the one-way ratchet portion of the housing and in the said standby mode.

According to the above-mentioned syringe, the cartridge sleeve comprises a cartridge body. The cartridge body has at least one viewing window formed in a peripheral wall of the cartridge body. A connection portion is formed at a rear end of the cartridge body. A positioning flange is formed on the peripheral wall of the cartridge body and located at a front end of the connection portion. Multiple engaging protrusions are formed on an outer peripheral surface of the connection portion. The front end of the housing is a cartridge sleeve connecting portion. Multiple L-shaped engaging grooves are formed in an inner peripheral wall of the cartridge sleeve connecting portion. Each L-shaped engaging groove includes a straight groove section being parallel to the central axis and a transverse section connected to a rear end of the straight groove section. When the connection portion at the rear end of the cartridge sleeve is inserted into the cartridge sleeve connecting portion at the front end of the housing, each engaging protrusion is able to slide along the straight groove section of a respective one of the L-shaped engaging grooves and to turn into an end of the transverse section of the respective one of the L-shaped engaging grooves to lock the cartridge sleeve to the front end of the housing.

According to the above-mentioned syringe, the housing has at least one spiral guiding rib formed on an inner peripheral wall of the housing. The spiral pushing assembly comprises a driving spiral tube, a clutch sleeve, and an output button. Wherein:

The driving spiral tube is mounted and is capable of spirally moving in the movable space of the housing. The driving spiral tube has a spiral tube channel formed through the driving spiral tube along the central axis, a guiding curved surface formed at a front segment of the spiral tube channel and converging forwardly along the central axis, a driving spiral guiding groove formed in an external peripheral wall of the driving spiral tube and screwed with the at least one spiral guiding rib of the housing, and a spiral tube rear end portion disposed at a rear end of the driving spiral tube. The spiral tube rear end portion extends to an outside of the rear end of the housing and blocked by the rear end of the housing.

The clutch sleeve is mounted in the spiral tube channel of the driving spiral tube and is able to move linearly relative to the driving spiral tube. The clutch sleeve has a sleeve body, multiple flexible locking claws formed at a front end of the sleeve body, and a connecting end portion disposed at a rear end of the sleeve body. A sleeve channel is formed in the sleeve body and extending along the central axis. At least one sleeve guide groove portion is formed on a peripheral wall of the sleeve channel and is parallel to the central axis. The multiple flexible locking claws have flexibility for radial expansion and contraction. When the clutch sleeve is moved frontward relative to the driving spiral tube, the multiple flexible locking claws are abutted by the guiding curved surface at a front end of the driving spiral tube and contract radially; and the multiple flexible locking claws are capable of bouncing backward to an original position along the guiding curved surface and expand.

The output button is disposed at an outside behind the rear end of the housing and is connected with the connecting end portion at a rear end of the clutch sleeve.

The metering guide sleeve is inserted in the driving spiral tube and the clutch sleeve and is able to be clamped by the multiple flexible locking claws of the clutch sleeve.

The total volume control nut has at least one flange rib formed on an outer peripheral surface of the total volume control nut and engaging with said at least one sleeve guide groove portion of the clutch sleeve.

According to the above-mentioned syringe, each of the flexible locking claws has a locking surface formed at an inner surface of the flexible locking claw. The locking surface of each of the flexible locking claws has multiple straight stripes extending along a front-to-back direction. The metering guide sleeve has an engaging surface formed on the outer peripheral surface, located between the guide sleeve front end portion and the guide sleeve threaded portion, of the guide sleeve body. The engaging surface has multiple straight stripes being parallel to the central axis and corresponding to the straight stripes of the locking surfaces of the flexible locking claws for engagement.

According to the above-mentioned syringe, the housing has a scale observing window formed at a rear section of an external peripheral wall of the housing; the driving spiral tube has a spiral scale portion formed on the external peripheral wall of the driving spiral tube and being parallel to the driving spiral guiding groove; the spiral scale portion has multiple scale lines able to be observed through the scale observing window of the housing.

The beneficial effect that can be achieved by the present invention is that when the syringe is in use, the front end of the injection mechanism is connected to the medicine vial, with the whole arrangement of the syringe, the injection mechanism can be manually triggered to covert between the injection mode and the standby mode. Wherein, when the diagonal tension knob of the injection mechanism is triggered to move backward, the multiple non-return ratchet buckles are driven to engage with the one-way ratchet portion of the housing to be in the injection mode to provide a function of quantitatively outputting medicament liquid. After the medicament liquid in the medicine vial is used up, the medicine vial is removed, the injection mechanism can be manually triggered to move the diagonal tension knob frontward. Whereby, the non-return ratchet buckles are disengaged from the one-way ratchet portion of the housing to be in the standby mode. So the metering screw can be directly manually pushed back to the default position. The metering guide sleeve is driven to rotate backwardly at the same time. The total volume control nut is moved back to the initial full position of the metering guide sleeve. Accordingly, the syringe can be reused.

The syringe of the present invention can further use the cartridge as a triggering component to convert the injection mechanism between the injection mode and the standby mode. The cartridge has functions of installing the medicine vial and the needle component. When the cartridge is mounted to the front end of the housing of the injection mechanism, the diagonal tension knob is pushed to automatically move backward to drive the multiple non-return ratchet buckles to engage with the one-way ratchet portion of the housing to be in the injection mode. When the cartridge is detached from the front end of the housing of the injection mechanism, the diagonal tension knob can move forward to allow the non-return ratchet buckles to disengage from the one-way ratchet portion of the housing to be in the standby mode.

The syringe of the present invention may further have the guiding ring in the front end of the housing. The guiding ring is spaced from the peripheral wall of the movable space. The at least one guiding block is formed on the inner annular surface of the guiding ring. The screw body of the metering screw has an axial guiding groove passing through the screw threaded portion and being parallel to the central axis. The axial guiding groove is engaged with the guiding block in the guiding ring of the housing. Thus, when the medicament liquid in the medicine vial is used up, the user detaches the cartridge with the medicine vial from the front end of the housing, the non-return ratchet buckles of the metering guide sleeve are disengaged from the one-way ratchet portion of the housing to release the unidirectional restriction, and the axial guiding groove of the metering screw can be aligned with the guiding block in the guiding ring of the housing. So the metering screw extending out from the housing can be quickly and directly pushed back to position along the central axis to drive the metering guide sleeve to rotate backwardly and to move the total volume control nut back to the initial full position of the metering guide sleeve along the central axis, thereby enhancing convenience of use.

The spiral pushing assembly of the syringe of the present invention may further comprise the driving spiral tube, the clutch sleeve, and the output button. Wherein, the driving spiral tube is spirally movably mounted in the housing. The front end segment of the spiral tube channel is formed as the guiding curved surface. The clutch sleeve is spirally moved in the spiral tube channel of the driving spiral tube. The rear end of the clutch sleeve extends out from the rear end of the housing and is connected with the output button. The clutch sleeve has the multiple flexible locking claws formed on the front end of the sleeve body thereof. The multiple flexible locking claws have flexibility for radial expansion and contraction. When the clutch sleeve is moved forward relative to the driving spiral tube, the multiple flexible locking claws are abutted against the guiding curved surface at the front end of the driving spiral tube to be radially contracted to clamp the metering guide sleeve. So the metering guide sleeve, the clutch sleeve, and the driving spiral tube can be rotated together. The multiple flexible locking claws can spring back to position along the guiding curved surface to expansion to release the metering guide sleeve. Accordingly, the metering guide sleeve is smoothly and reliably engaged with and disengaged from the metering guide sleeve.

The syringe of the present invention may further have the scale observing window formed at the external peripheral wall of the housing. The driving spiral tube has a spiral scale portion formed on the external peripheral wall of the driving spiral tube and being parallel to the driving spiral guiding groove. The spiral scale portion has multiple scale lines observed through the scale observing window of the housing. So the driving spiral tube as a single component have functions of driving and dose scale display.

BRIEF DESCRIPTION OF THE DRAWINGS

The following drawings are only intended to illustrate and explain the present invention, and do not limit the scope of the present invention. Wherein.

DETAILED DESCRIPTION OF PREFERRED EMBODIMENTS

The following describes the technical means adapted by the present invention to achieve the intended purpose of the invention in conjunction with the drawings and the preferable embodiments of the present invention.

Figure 1:
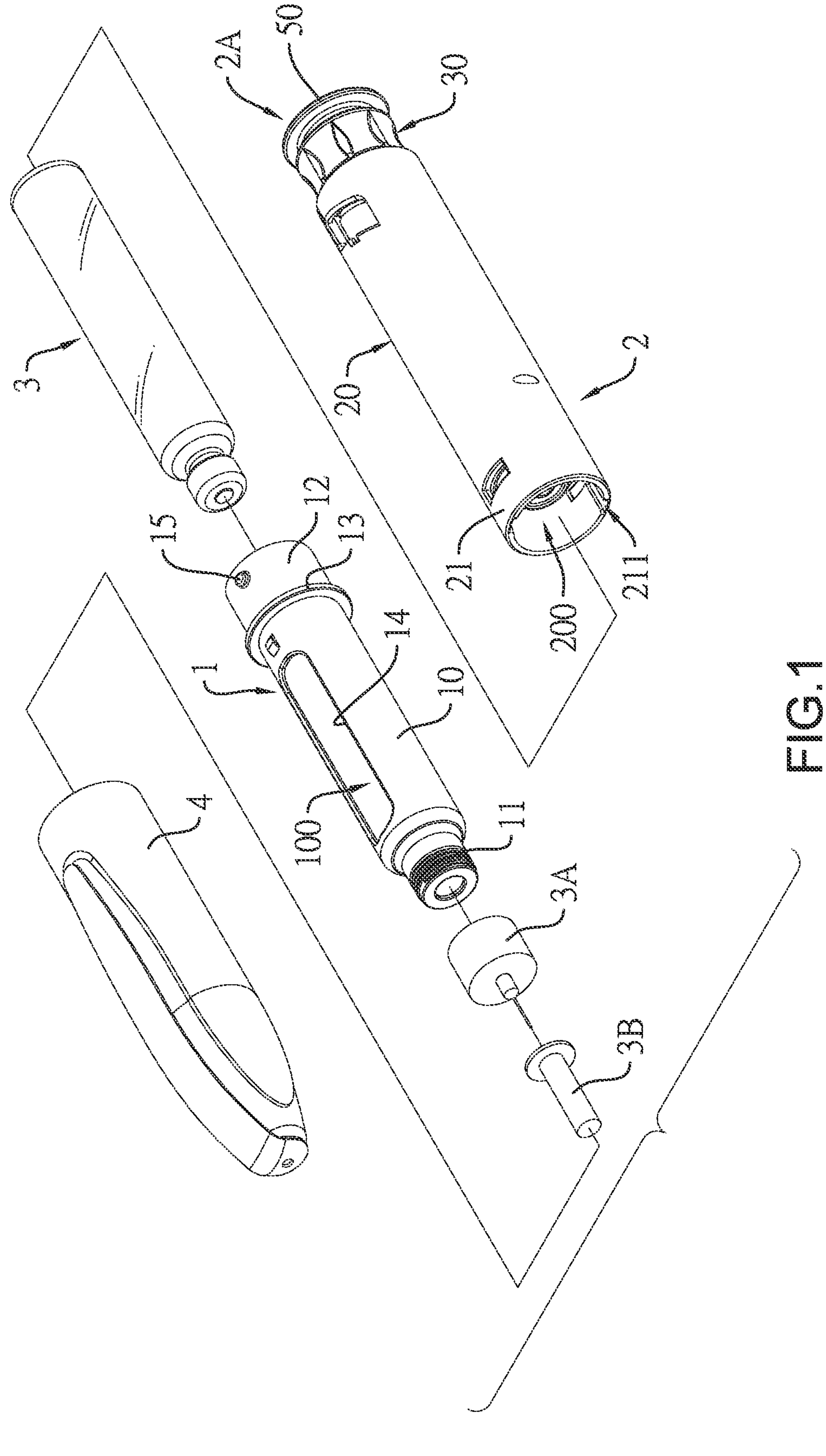
FIG. 1 is an exploded perspective view of a preferable embodiment of a syringe in accordance with the present invention and a medicine vial and a needle component, showing that the syringe uses a cartridge sleeve as a triggering component.
Figure 2:
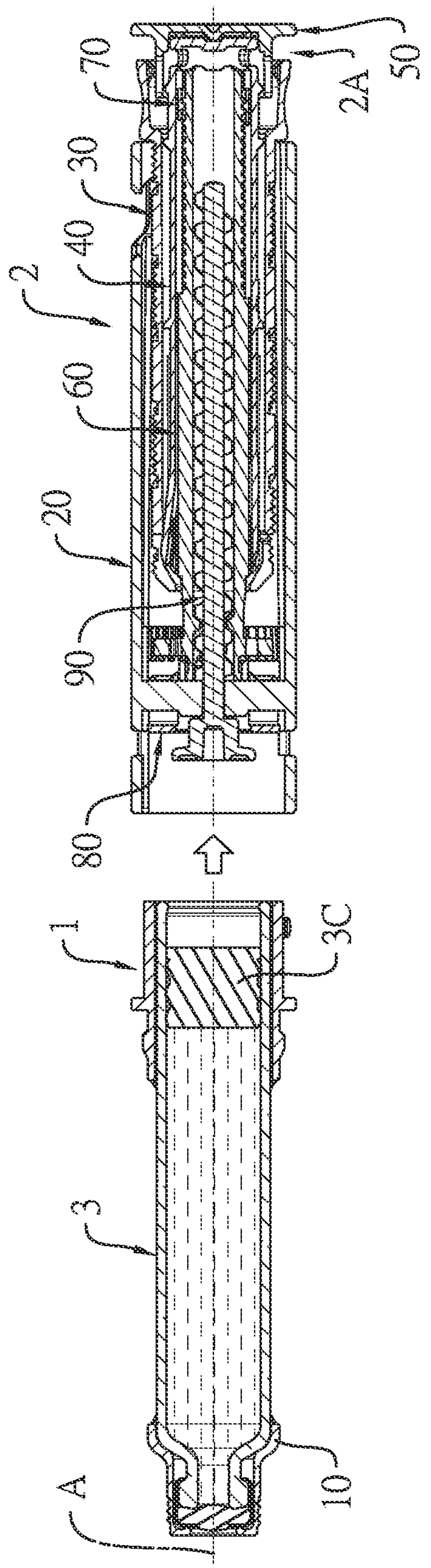
FIG. 2 is a cross sectional side view of the preferable embodiment of the syringe in FIG. 1 showing that the cartridge sleeve is connected to the medicine vial and is disconnected from an injection mechanism.

With reference to FIGS. 1 and 2, according to the content of the invention disclosed above, the syringe in accordance with the present invention is able to be assembled with a medicine vial 3 containing medicament liquid and a needle component 3A connected to a front end of the medicine vial 3 to provide a device adapted to perform function of medicament liquid injection. The medicine vial 3 and the needle component 3A are both conventional components. The medicine vial 3 contains the medicament liquid and has a piston 3C mounted therein for pushing and outputting the medicament liquid.

As shown in FIGS. 1 and 2 the syringe in accordance with the present invention mainly comprises an injection mechanism 2. The injection mechanism 2 has an injection mode and a standby mode. The injection mechanism 2 can be directly manually triggered through a user's hands or indirectly manually triggered through a triggering component to perform a conversion between the injection mode and the standby mode.

In the preferable embodiment shown in FIGS. 1 and 2, the syringe uses a cartridge sleeve 1 as a triggering component to convert the modes of the injection mechanism 2. The injection mechanism 2 is triggered to covert from the standby mode to the injection mode via connecting the cartridge sleeve 1 to the front end of the injection mechanism 2. When the cartridge sleeve 1 is detached from the front end of the injection mechanism 2, the injection mechanism 2 automatically converts to the standby mode. However, the triggering component to convert the modes of the injection mechanism 2 is not limited to the cartridge sleeve 1 in the syringe of the present invention.

For convenience of illustration of the specific structure of the syringe of the present invention, the preferable embodiment shown in FIGS. 1 and 2 is taken as an example for illustration. The syringe of the present invention defines a central axis A extending along a front-to-back direction of the syringe. The injection mechanism 2 comprises a housing 20, a spiral pushing assembly 2A, a metering guide sleeve 60, a total volume control nut 70, a diagonal tension knob 80, and a metering screw 90. The structure of each of the aforementioned components is illustrated below.

As shown in FIGS. 1 to 5 and 6 to 8, the housing 20 has a movable space 200 formed through the housing 20 along the central axis A. A one-way ratchet portion 23 is formed inside the movable space 200 of the housing 20. The one-way ratchet portion 23 has multiple unidirectional angled ratchet teeth. The multiple unidirectional angled ratchet teeth are in a rotational and symmetric arrangement with respect to a predetermined forward direction of the central axis A. The front end of the housing 20 is detachably connected to the medicine vial 3.

As shown in FIGS. 1 to 5 and 6 to 8, the housing 20 has a guiding ring 22 formed in the movable space 200 and located in front of the one-way ratchet portion 23. The guiding ring 22 is spaced from a peripheral wall of the movable space 200. In the preferable embodiment, an outer peripheral surface of the guiding ring 22 and the peripheral wall of the movable space 200 are connected to each other via multiple arms 24, so the guiding ring 22 is kept spaced from the peripheral wall of the movable space 200 by a predetermined distance. At least one guiding block 221 is formed on an inner annular wall of the guiding ring 22. In the preferable embodiment, the inner annular wall of the guiding ring 22 has two guiding blocks 221 being radially symmetric with respect to the central axis A. The housing 20 has one or multiple spiral guiding ribs 25 formed in the movable space 200 and at a rear segment of the inner peripheral wall of the housing 20.

As shown in FIGS. 2 to 4 and 6 to 10, the spiral pushing assembly 2A is mounted in the movable space 200 of the housing 20 and is capable of spirally moving around the central axis A. The spiral pushing assembly 2A extends out from a rear end of the housing 20 and is able to be pushed to generate a spiral propulsion. In the preferable embodiment, the spiral pushing assembly 2A comprises a driving spiral tube 30, a clutch sleeve 40, and an output button 50.

As shown in FIGS. 2 to 4 and 6 to 10, the driving spiral tube 30 is mounted in the movable space 200 of the housing 20 and is capable of spirally moving. The driving spiral tube 30 has a spiral tube channel 31 formed through the driving spiral tube 30 along the central axis A. A guiding curved surface 32 is formed at a front segment of the spiral tube channel 31 and converges forwardly along the central axis A. That is, the spiral tube channel 31 at the front segment of the driving spiral tube 30 is formed as a curved surface having an opening gradually decreased from the rear to the front thereof. A driving spiral guiding groove 33 is formed in an external peripheral wall of the driving spiral tube 30. The pitch of the driving spiral guiding groove 33 is set according to the volume of the predetermined dose of the medicament liquid of the syringe. And the driving spiral guiding groove 33 is screwed with the spiral guiding ribs 25 in the housing 20. The driving spiral tube 30 has a spiral tube rear end portion 34 with a larger diameter and disposed at a rear end of the driving spiral tube 30. The spiral tube rear end portion 34 extends out from the rear end of the housing 20 and can be blocked by the rear end of the housing 20 to limit its moving path.

Figure 3:
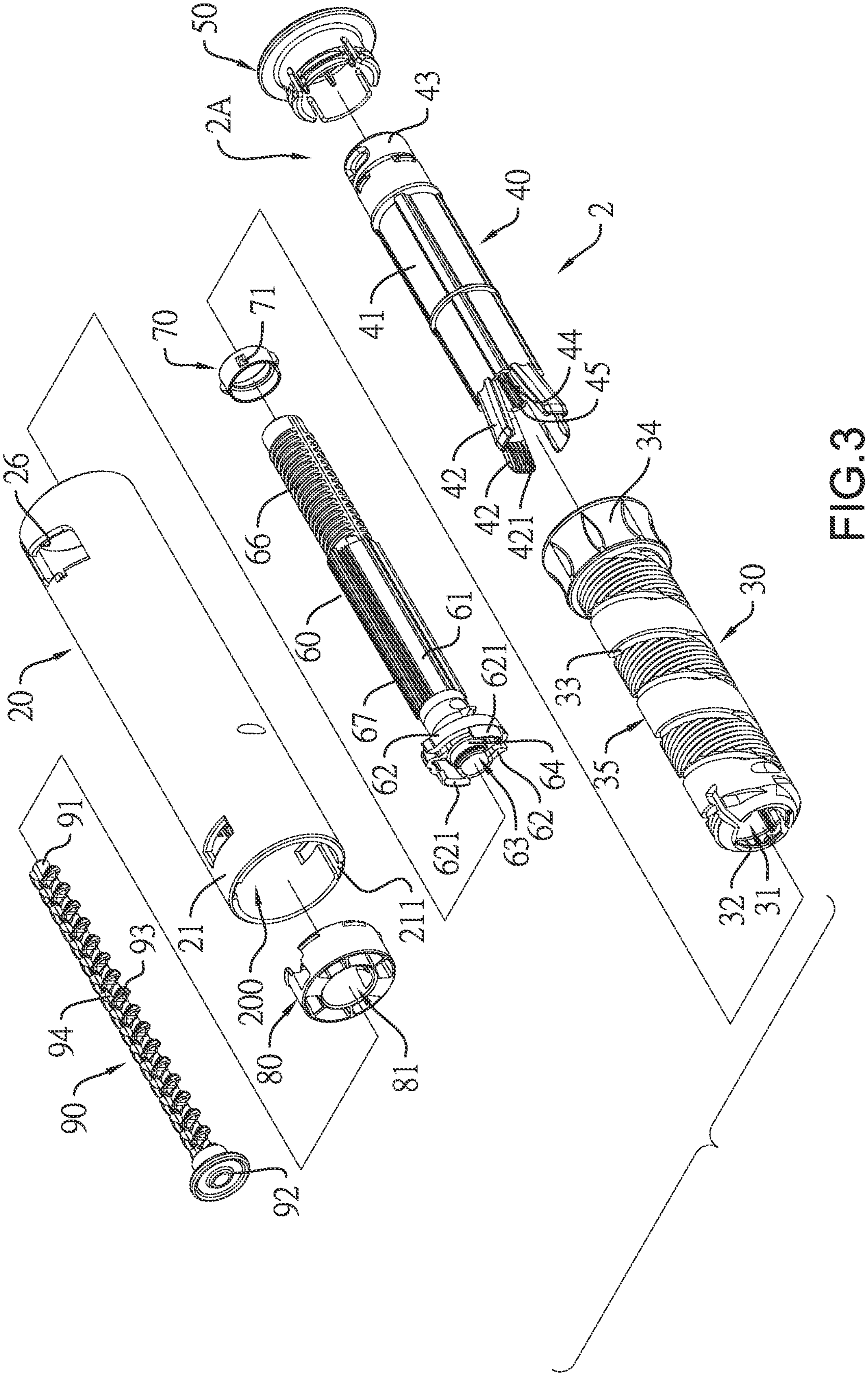
FIG. 3 is an exploded perspective view of the injection mechanism in FIGS. 1 and 2.
Figure 4:
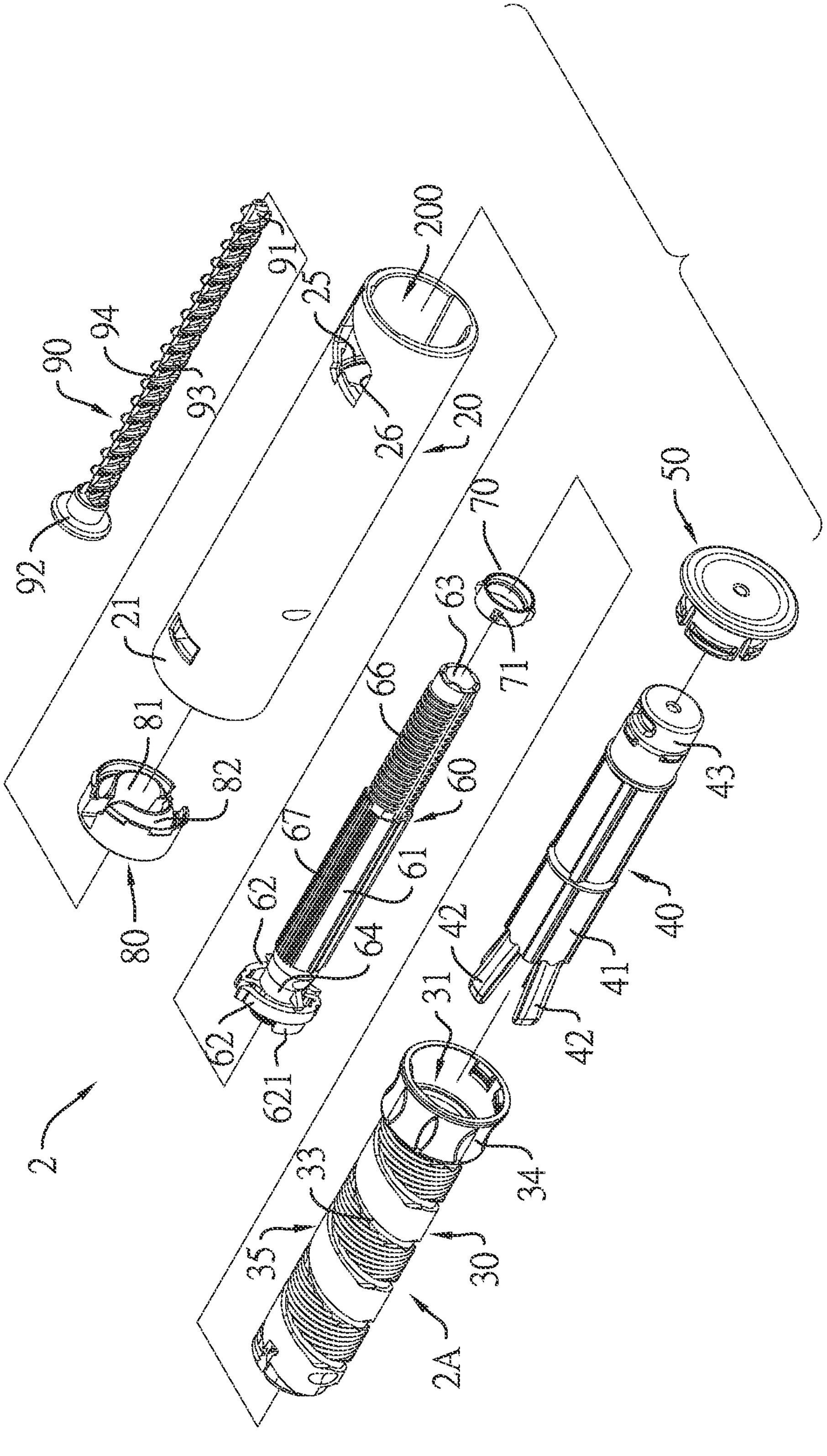
FIG. 4 is another exploded perspective view of the injection mechanism in FIGS. 1 and 2.
Figure 5:
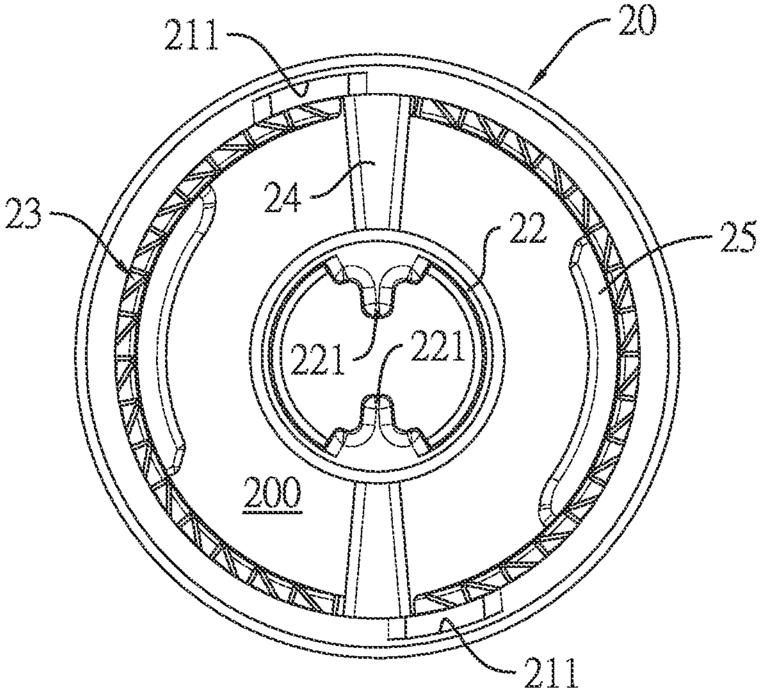
FIG. 5 is a front view of a housing of the injection mechanism in FIGS. 3 and 4.
Figure 6:
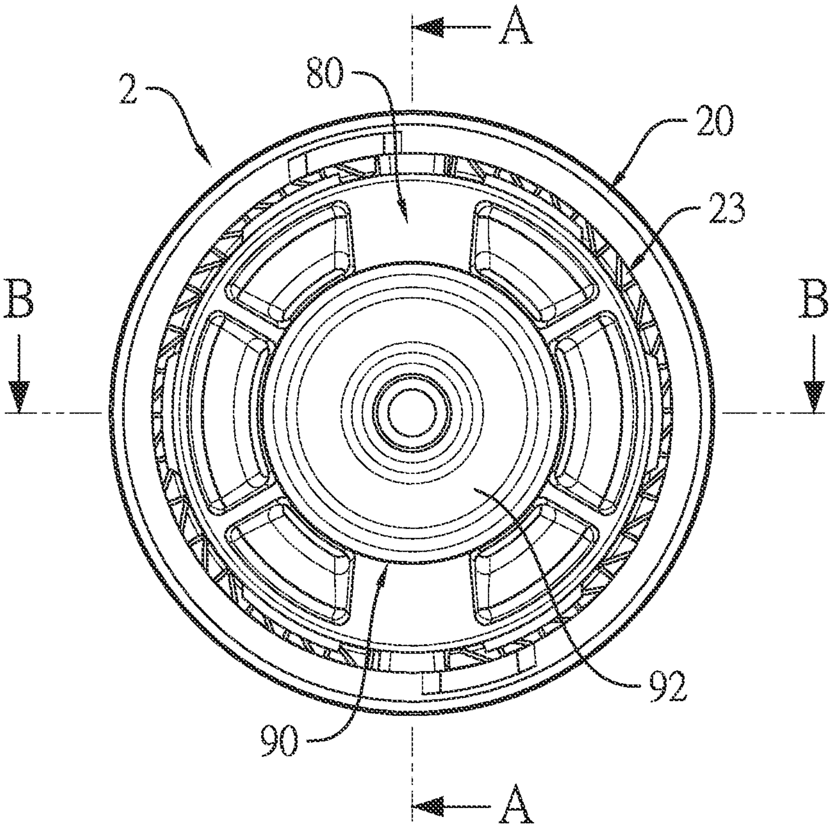
FIG. 6 is a front view of the injection mechanism in FIGS. 3 and 4.
Figure 7:
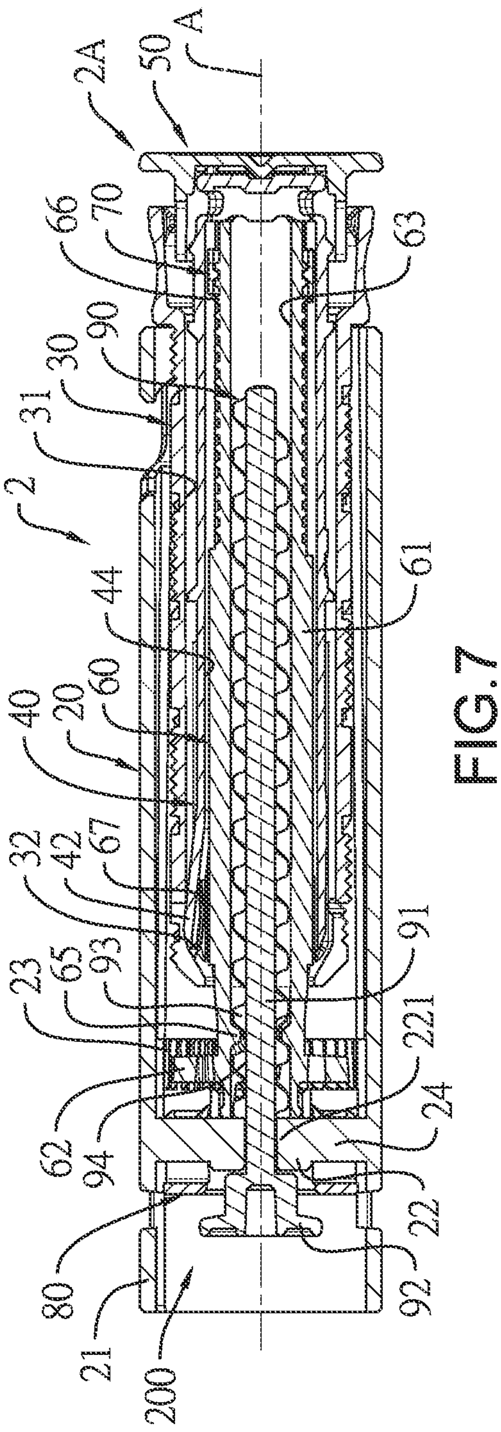
FIG. 7 is a cross sectional side view along line A-A in FIG. 6.
Figure 8:
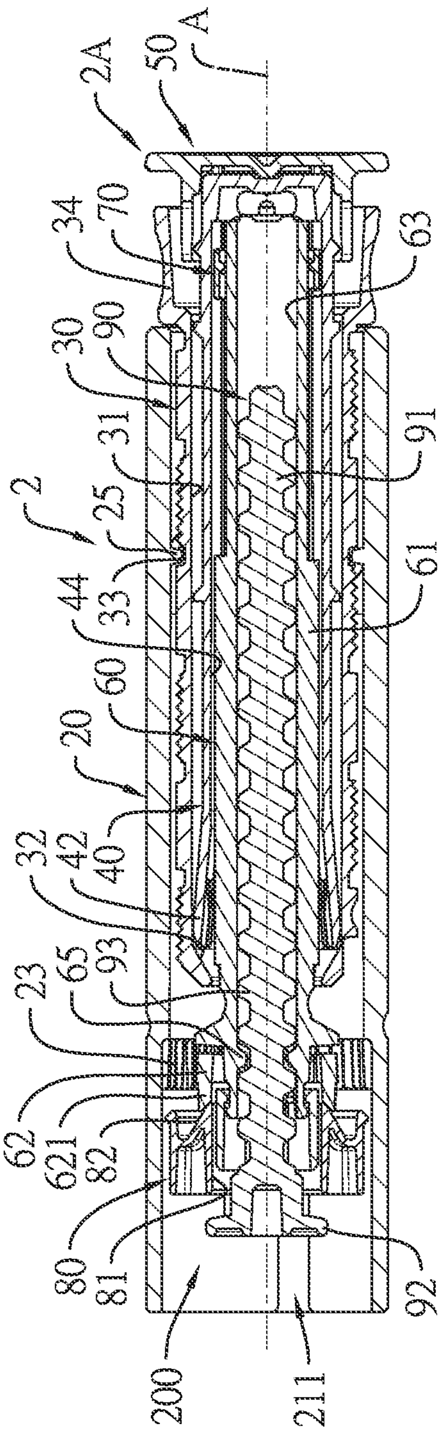
FIG. 8 is a cross sectional side view along line B-B in FIG. 6.
Figure 9:
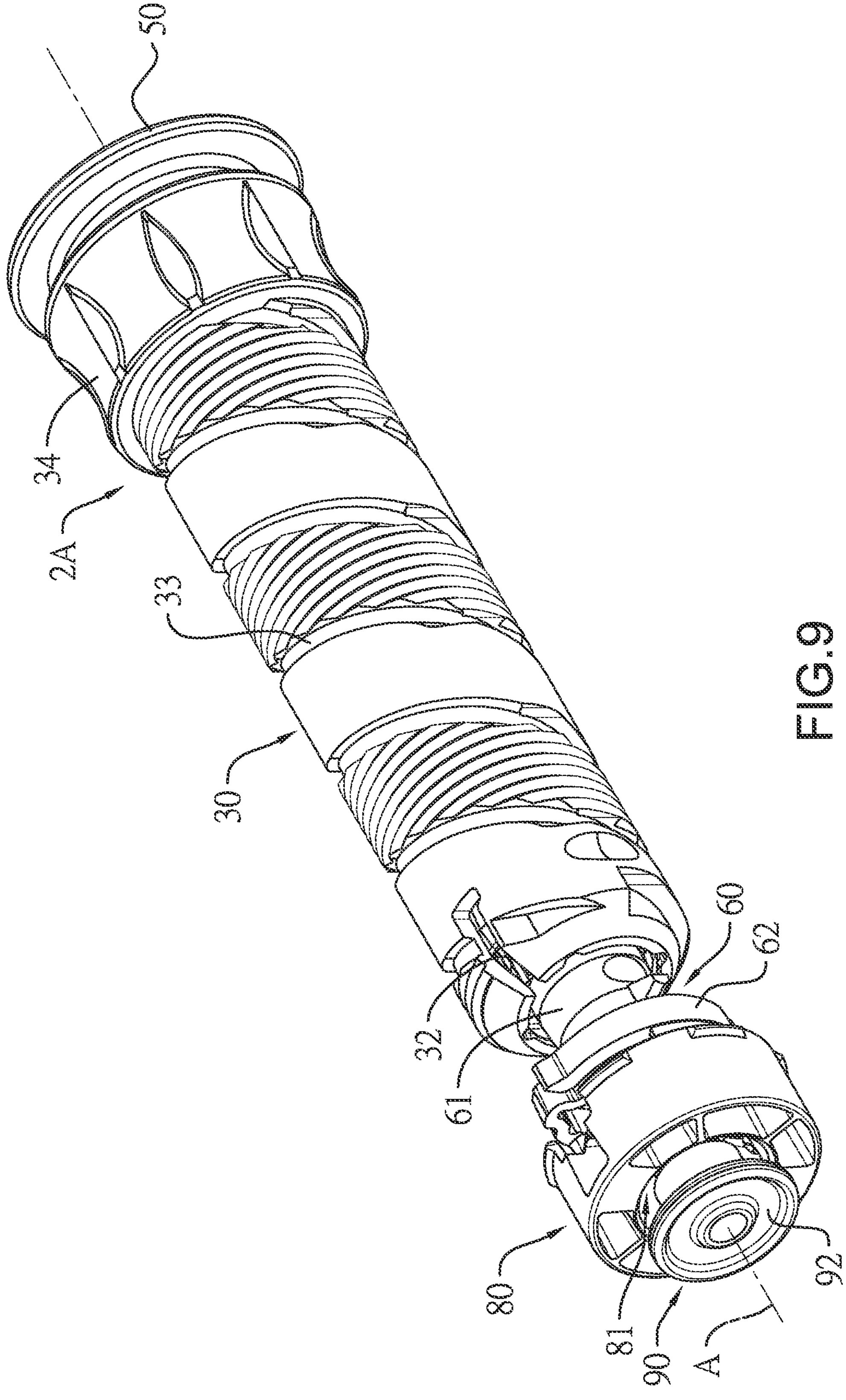
FIG. 9 is a perspective view of the injection mechanism in FIGS. 3 and 4, wherein the housing is removed.
Figure 10:
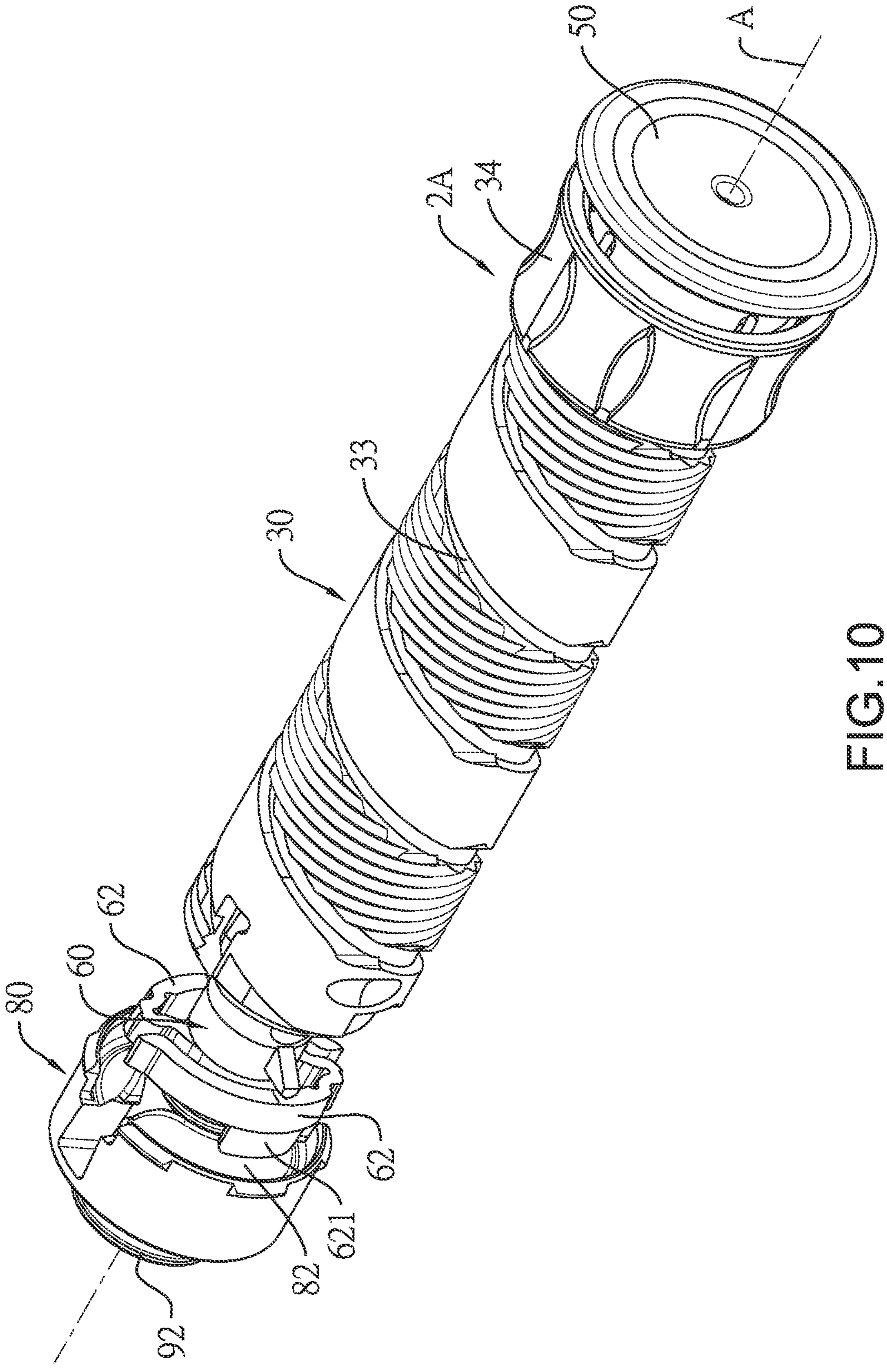
FIG. 10 is another perspective view of the injection mechanism in FIGS. 3 and 4, wherein the housing is removed.
Figure 11:
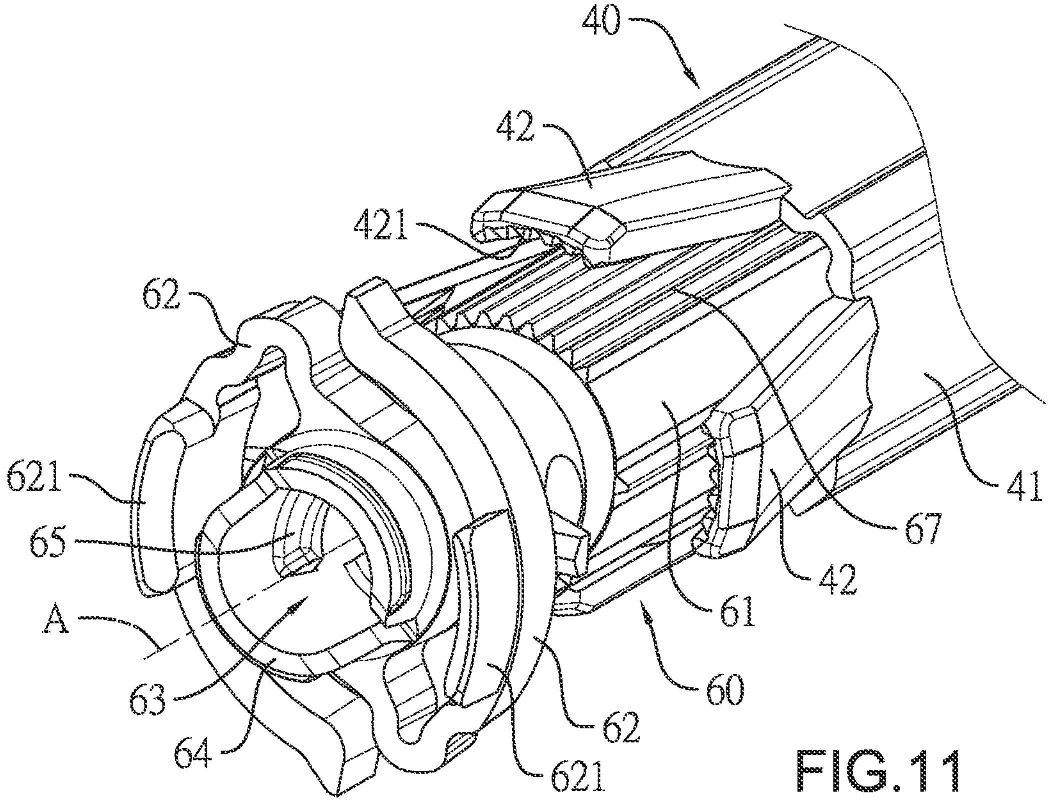
FIG. 11 is a partial perspective view of a clutch sleeve of the injection mechanism in FIGS. 3 and 4 showing the clutch sleeve assembled with a metering guide sleeve.
Figure 12:
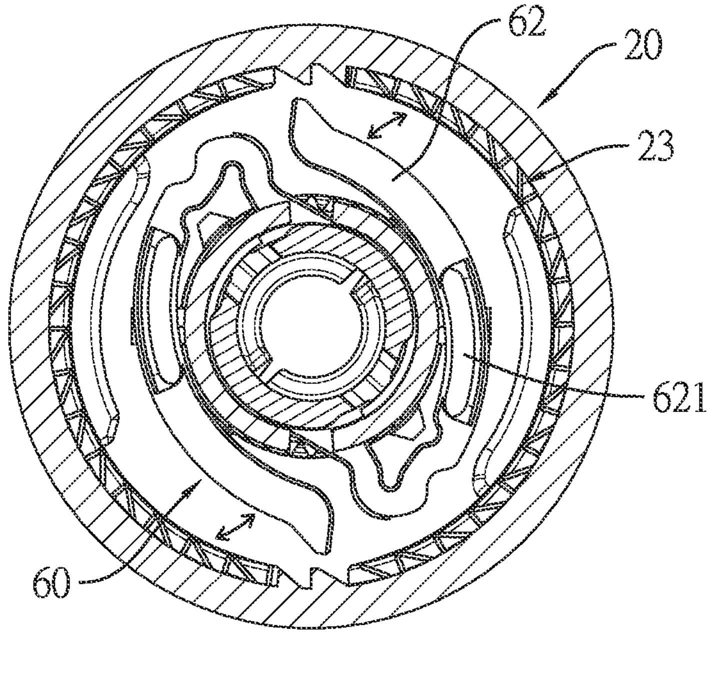
FIG. 12 is a cross sectional front view of the housing of the injection mechanism in FIGS. 3 and 4 showing the clutch sleeve assembled with the metering guide sleeve.
Figure 13:
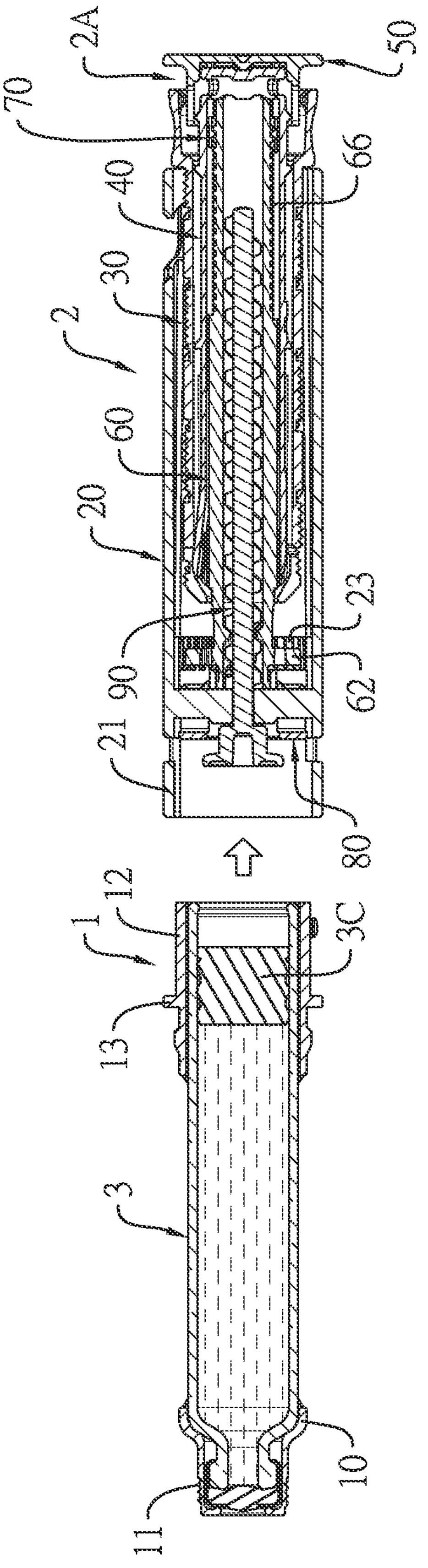
FIG. 13 is an operational cross sectional side view of the preferable embodiment of the syringe in FIG. 1 showing that the cartridge sleeve is connected to the medicine vial and is disconnected from the injection mechanism.
Figure 14:
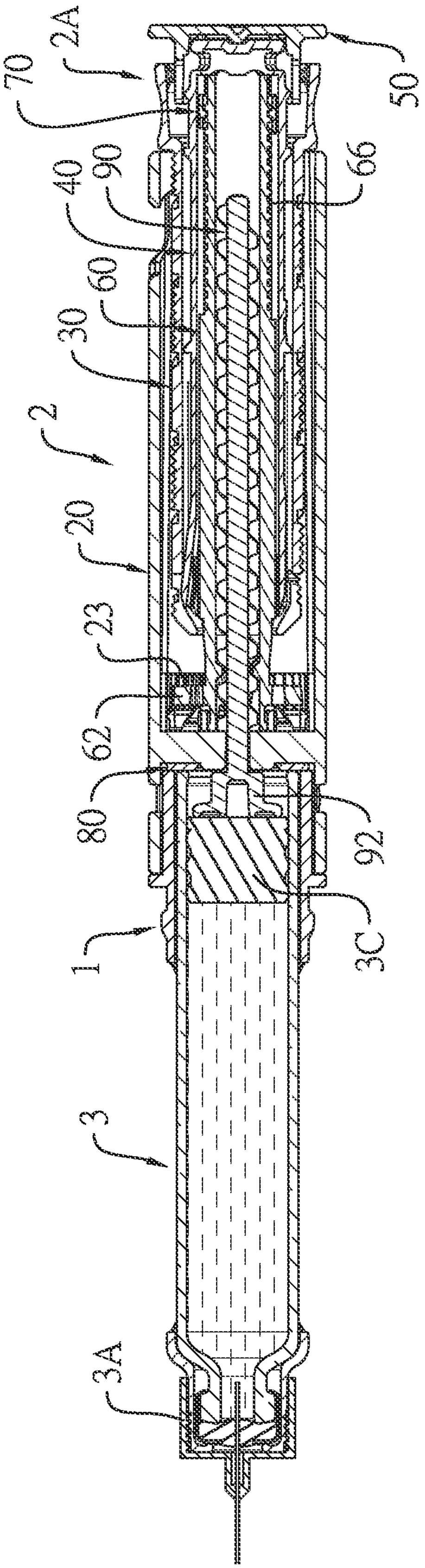
FIG. 14 is an operational cross sectional side view of the preferable embodiment of the syringe in FIG. 13 showing that the cartridge sleeve connected with the medicine vial and the needle component is assembled to a front end of the injection mechanism.
Figure 15:
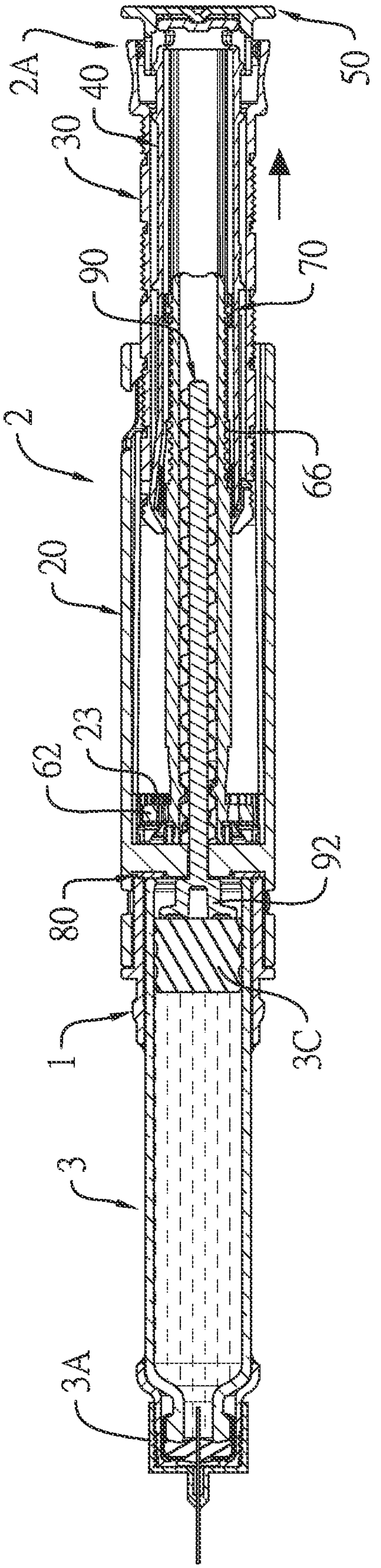
FIG. 15 is an operational cross sectional side view of the injection mechanism in FIG. 14, showing that a spiral pushing assembly of the injection mechanism is pulled out from a rear end of the housing.
Figure 16:
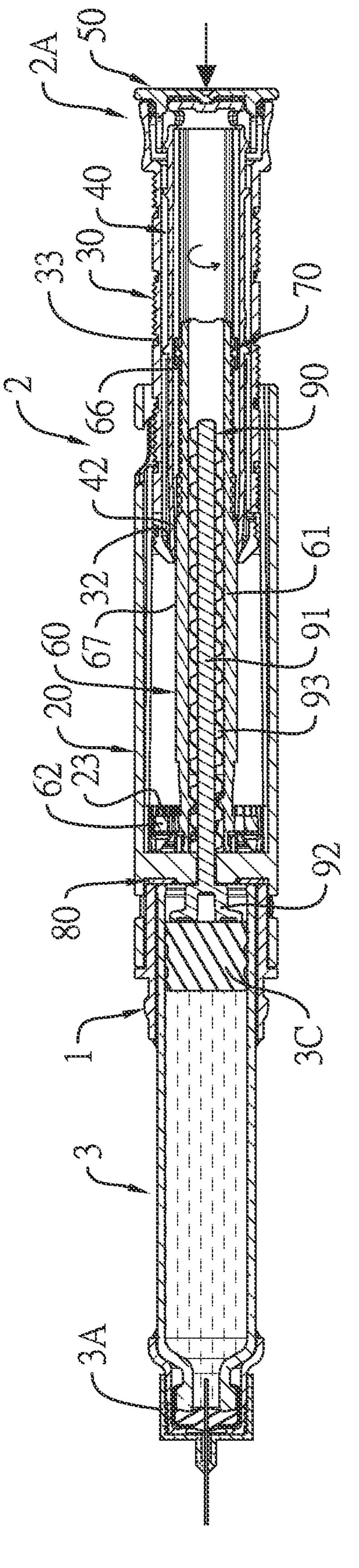
FIG. 16 is an operational cross sectional side view of the injection mechanism in FIG. 15, showing that the spiral pushing assembly of the injection mechanism is pushed frontward to output medicament liquid for injection.
Figure 17:
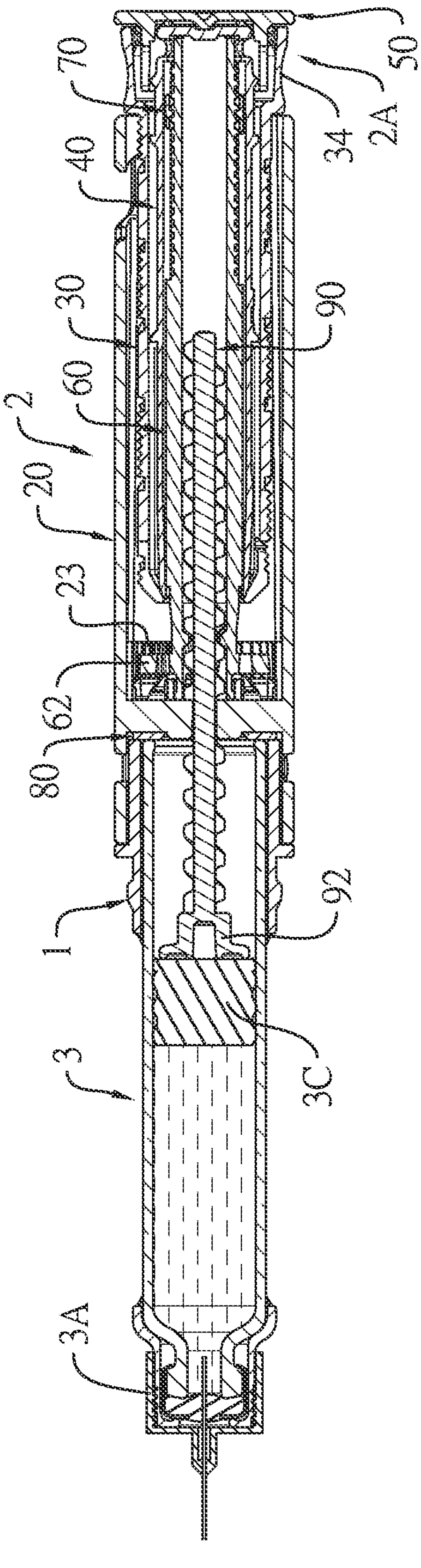
FIG. 17 is an operational cross sectional side view of the injection mechanism in FIG. 16, shown after one time injection.
Figure 18:
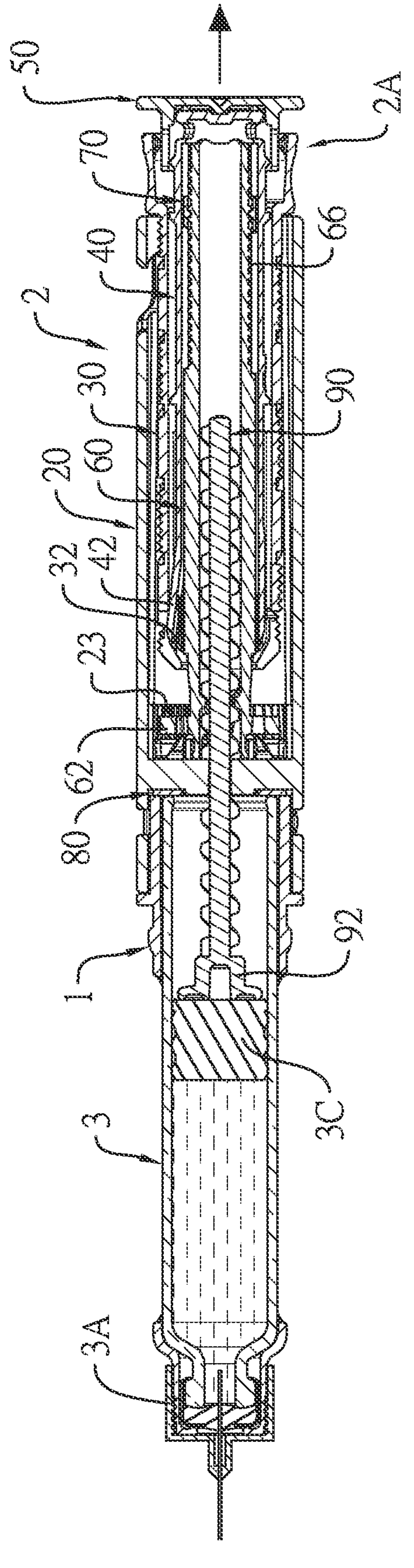
FIG. 18 is an operational cross sectional side view of the injection mechanism in FIG. 17, showing that the spiral pushing assembly of the injection mechanism is pulled out from the rear end of the housing again.
Figure 19:
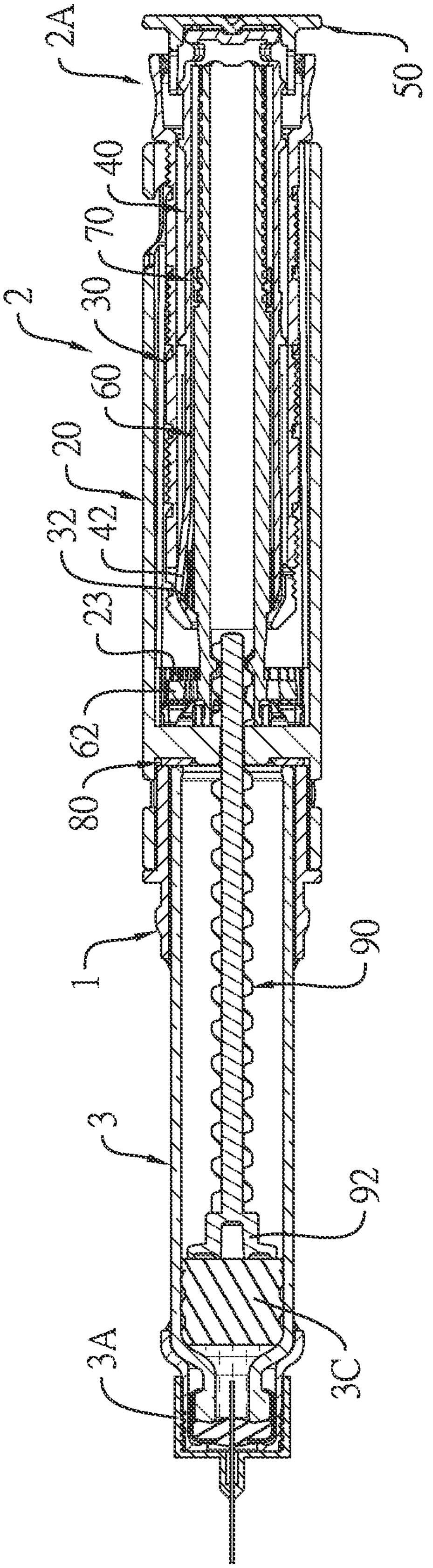
FIG. 19 is an operational cross sectional side view of the syringe in accordance with the present invention showing that the medicament liquid in the medicine vial is used up.
Figure 20:
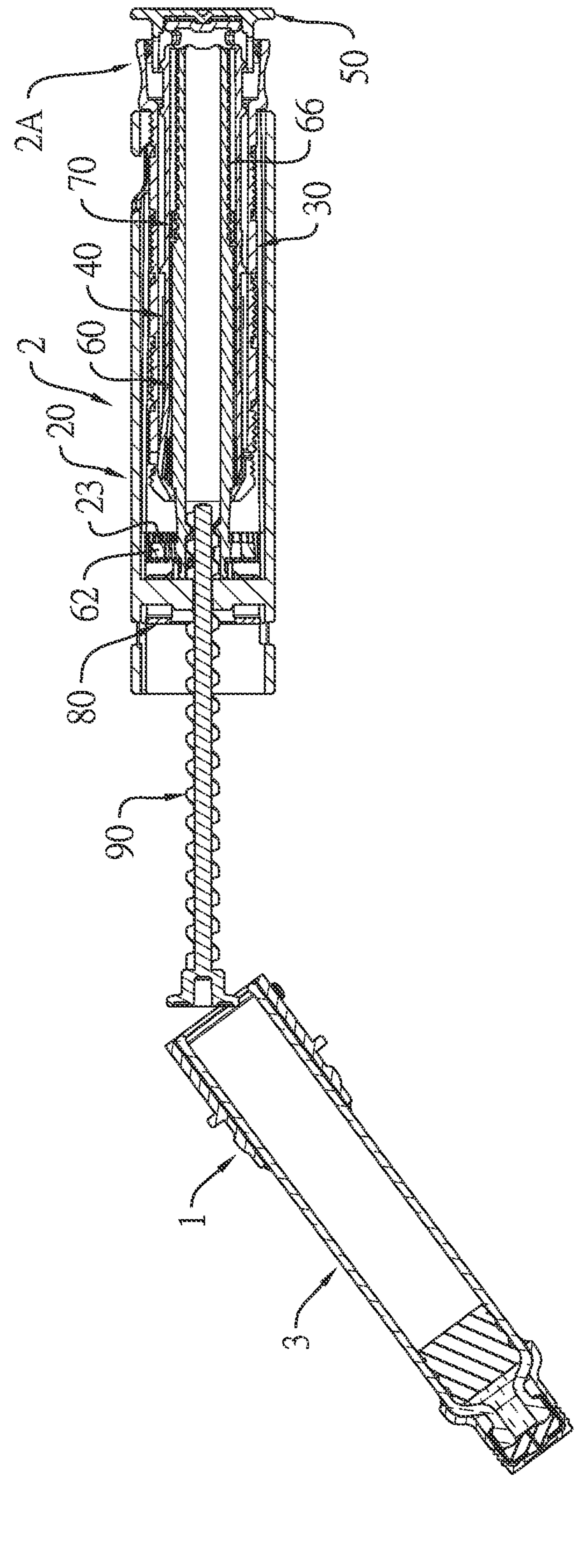
FIG. 20 is an operational cross sectional side view of the syringe in FIG. 19 showing that the empty medicine vial and the cartridge sleeve around the medicine vial are detached from the front end of the injection mechanism.
Figure 21:
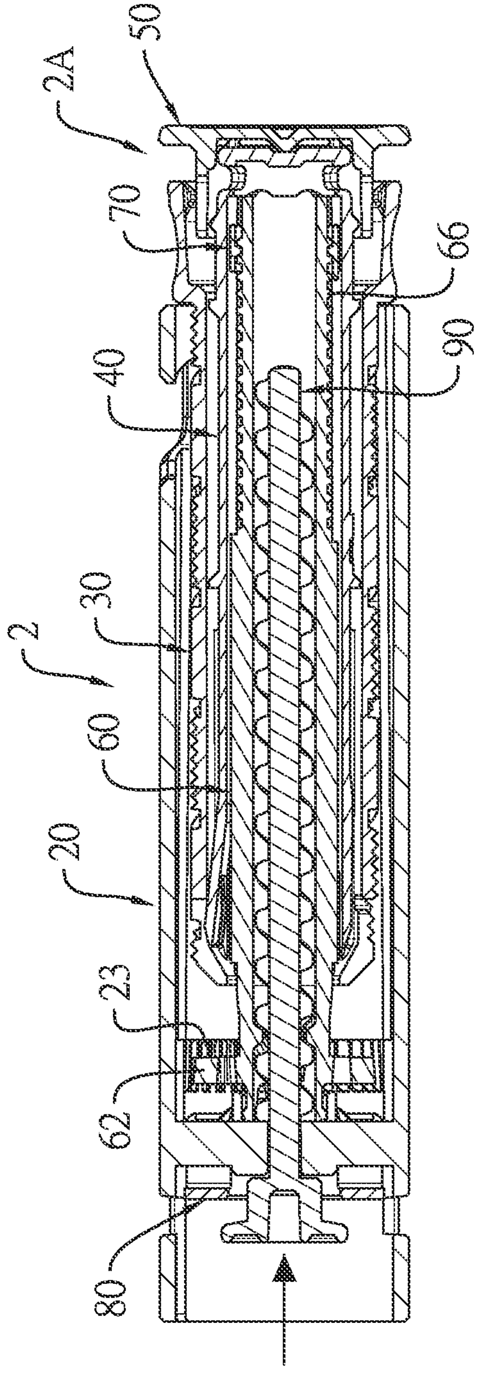
FIG. 21 is an operational cross sectional side view of the injection mechanism in FIG. 20 showing that the metering screw of the injection mechanism is pushed back to make the injection mechanism return to a start condition.

As shown in FIGS. 3 and 4, a scale observing window 26 is formed through an external peripheral wall of the housing 20. A spiral scale portion 35 is formed on the external peripheral wall of the driving spiral tube 30 and is parallel to the driving spiral guiding groove 33. The spiral scale portion 35 has multiple scale lines (not shown in the drawings). The scale lines of the spiral scale portion 35 can be observed through the scale observing window 26 of the housing 20 and make the driving spiral tube 30 have functions of driving and dose scale display.

As shown in FIGS. 2 to 4 and 6 to 8, the clutch sleeve 40 is mounted in the spiral tube channel 31 of the driving spiral tube 30 and able to linearly move relative to the driving spiral tube 30. The clutch sleeve 40 has a sleeve body 41, multiple flexible locking claws 42 formed at a front end of the sleeve body 41, and a connecting end portion 43 formed at a rear end of the sleeve body 41. A sleeve channel 44 is formed in the sleeve body 41 and forwardly extends along the central axis A. At least one sleeve guide groove portion 45 is formed on a peripheral wall of the sleeve channel 44 and is parallel to the central axis A. The multiple flexible locking claws 42 have flexibility for radial expansion and contraction. When the clutch sleeve 40 moves frontward relative to the driving spiral tube 30, the multiple flexible locking claws 42 are abutted against the guiding curved surface 32 at a front end of the driving spiral tube 30 to radially contract and are capable of bouncing backward to an original position along the guiding curved surface 32 to expand. In the preferable embodiment, each flexible locking claw 42 has a locking surface 421 disposed at an inner surface of the flexible locking claw 42. The locking surface 421 has multiple straight stripes extending along the front-to-back direction.

The output button 50 is disposed outside the rear end of the housing 20 and is pivotally connected with the connecting end portion 43 at a rear end of the clutch sleeve 40. The output button 50 is adapted to provide an operational component for the user.

As shown in FIGS. 2 to 4 and 6 to 11, the metering guide sleeve 60 is mounted in the housing 20, is capable of rotating at a fixing point, is inserted in the driving spiral tube 30 and the clutch sleeve 40, and is selectively clamped by the multiple flexible locking claws 42 of the clutch sleeve 40. When the flexible locking claws 42 of the clutch sleeve 40 are driven to contract by the guiding curved surface 32 of the driving spiral tube 30 to clamp the metering guide sleeve 60, the metering guide sleeve 60, the clutch sleeve 40, and the driving spiral tube 30 are able to rotate together. The metering guide sleeve 60 comprises a guide sleeve body 61 and multiple non-return ratchet buckles 62. The guide sleeve body 61 has a guide sleeve central hole 63 formed through the guide sleeve body 61 along the central axis A. The guide sleeve body 61 has a guide sleeve front end portion 64 formed at a front end of the guide sleeve body 61. The guide sleeve front end portion 64 is pivotally connected within the guiding ring 22 of the housing 20. At least one spiral portion 65 is formed on an inner peripheral wall of the guide sleeve central hole 63 at a segment thereof with respect to the guide sleeve front end portion 64. A guide sleeve threaded portion 66 is formed on a rear segment of an outer peripheral surface of the guide sleeve body 61. The guide sleeve threaded portion 66 has a pitch being smaller than the pitch of the driving spiral guiding groove 33 of the driving spiral tube 30. An engaging surface 67 is formed on the outer peripheral surface of the guide sleeve body 61 and is located between the guide sleeve front end portion 64 and the guide sleeve threaded portion 66. The engaging surface 67 has multiple straight stripes being parallel to the central axis A and corresponding to the straight stripes formed in the locking surfaces 421 of the flexible locking claws 42 for engagement. The multiple non-return ratchet buckles 62 are formed on an external surface of the guide sleeve front end portion 64. The multiple non-return ratchet buckles 62 are all curved and are in a rotational symmetric arrangement with respect to the forward direction of the central axis A. The multiple non-return ratchet buckles 62 can be controlled to engage with or disengage from the one-way ratchet portion 23 of the housing 20. When the non-return ratchet buckles 62 engage with the one-way ratchet portion 23 of the housing 20, the metering guide sleeve 60 can only rotate forwardly and cannot rotate backwardly, that is, in the injection mode. When the non-return ratchet buckles 62 disengage from the one-way ratchet portion 23 of the housing 20, the non-return function is released, so the metering guide sleeve 60 can freely rotate forwardly or backwardly, that is, in the standby mode. In the preferable embodiment, each non-return ratchet buckle 62 has a wing 621 protruding forwardly from a front end surface thereof.

As shown in FIGS. 2 to 4 and 6 to 8, the total volume control nut 70 is mounted in the spiral tube channel 31 of the driving spiral tube 30, is capable of linearly moving along the central axis A, and is screwed with the metering guide sleeve 60. A total movable distance of the total volume control nut 70 relative to the guide sleeve threaded portion 66 of the metering guide sleeve 60 corresponds to a movable distance of the piston 3C in the medicine vial 3 to control a total output volume of the medicament liquid in the medicine vial 3. In the preferable embodiment, the total volume control nut 70 has an inner threaded hole and is screwed with the guide sleeve threaded portion 66 at the rear segment of the guide sleeve body 61 of the metering guide sleeve 60. The total volume control nut 70 has flange ribs 71 formed on an outer peripheral surface thereof. The flange ribs 71 engage with the sleeve guide groove portion 45 in the sleeve channel 44 of the clutch sleeve 40.

As shown in FIGS. 2 to 4 and 6 to 10, the diagonal tension knob 80 is mounted in the front end of the housing 20 and is movable along the central axis A. The diagonal tension knob 80 can be driven to convert the engagement and the disengagement between the non-return ratchet buckles 62 and the one-way ratchet portion 23 of the housing 20 for conversion between the injection mode and the standby mode.

In the preferable embodiment, the diagonal tension knob 80 is mounted in the cartridge sleeve connecting portion 21 at the front end of the housing 20, through the space between the peripheral wall of the movable space 200 and the outer annular surface of the guiding ring 22, and has an inner hole 81 formed through the diagonal tension knob 80 along the central axis A. The diagonal tension knob 80 has a conical surface 82 having diameters gradually increasing forwardly. A rear section of the conical surface 82 abuts the wings 621 of the non-return ratchet buckles 62. When the diagonal tension knob 80 is forced to move backward, the diagonal tension knob 80 can drive the non-return ratchet buckles 62 of the metering guide sleeve 60 to expand radially by a radial and diagonal pushing force of the conical surface 82, and the non-return ratchet buckles 62 and one-way ratchet portion 23 of the housing 20 engage with each other. When the diagonal tension knob 80 is force free, the non-return ratchet buckles 62 contract through their own elasticity to disengage from the one-way ratchet portion 23 of the housing 20 and push the conical surface 82 of the diagonal tension knob 80 and make the diagonal tension knob 80 move forwardly to restore.

As shown in FIGS. 2 to 4 and 6 to 10, the metering screw 90 is inserted in the diagonal tension knob 80 and the guiding ring 22 of the housing 20. The metering screw 90 is screwed within the metering guide sleeve 60 and is able to be driven to move linearly along the central axis A. The metering screw 90 comprises a screw body 91 and a screw front end portion 92 formed at a front end of the screw body 91. A screw threaded portion 93 is formed on an outer peripheral surface of the screw body 91 and has at least one axial guiding groove 94 being parallel to the central axis A and passing through the screw threaded portion 93. The screw threaded portion 93 is screwed with the spiral portion 65 inside the guide sleeve front end portion 64 of the metering guide sleeve 60. Said axial guiding grooves 94 are engaged with the guiding blocks 221 inside the guiding ring 22 of the housing 20. The screw front end portion 92 is located in front of the guiding ring 22 of the housing 20 and in front of the diagonal tension knob 80. A spiral movement of the metering guide sleeve 60 drives the metering screw 90 in the housing 20 to move linearly along the central axis A to push the piston 3C in the medicine vial 3 to preform quantitative output of the medicament liquid in the medicine vial 3. When the injection mechanism 2 is in the standby mode, the metering screw 90 extending out from the front end of the housing 20 can linearly move along the central axis A backwardly and be received into the housing 20.

When the syringe of the present invention uses the cartridge sleeve 1 as a triggering component to convert the modes of the injection mechanism 2, as shown in FIGS. 1 and 2, the cartridge sleeve 1 contains the medicine vial 3 and the needle component 3A assembled with the medicine vial 3 and is detachably connected to the injection mechanism 2. In the preferable embodiment, the cartridge sleeve 1 has a containing space 100 formed therethrough along the central axis A. And the cartridge sleeve 1 has a cartridge body 10. The cartridge body 10 has a needle connecting portion 11 formed at a front end of the cartridge body 10 and a connection portion 12 formed at a rear end of the cartridge body 10. The containing space 100 has two openings respectively formed through the front end and the rear end of the cartridge sleeve 1. The medicine vial 3 is detachably mounted and fixed in the containing space 100 of the cartridge sleeve 1. The needle component 3A is detachably sleeved on the needle connecting portion 11. The connection portion 12 at the rear end of the cartridge body 10 is detachably connected to the injection mechanism 2.

As shown in FIGS. 1 to 5 and 6 to 8, in the preferable embodiment, the needle connecting portion 11 has a thread formed on an outer peripheral surface thereof. The needle component 3A is screwed with the needle connecting portion 11. The cartridge body 10 has a positioning flange 13 formed on a peripheral wall thereof and located at a front end of the connection portion 12. One or multiple viewing windows 14 may be formed in the peripheral wall of the cartridge body 10 and communicate with the containing space 100 to allow a user to observe the volume of the remaining medicament liquid in the medicine vial 3 in the cartridge sleeve 1.

As shown in FIGS. 1 to 5 and 6 to 8, the front end of the housing 20 has a cartridge sleeve connecting portion 21. The connection portion 12 at the rear end of the cartridge sleeve 1 is detachably connected to the cartridge sleeve connecting portion 21 of the housing 20. The connecting structures between the cartridge sleeve connecting portion 21 at the front end of the housing 20 and the connection portion 12 at the rear end of the cartridge sleeve 1 can be engagement structures or threaded connection structures. In the preferable embodiment, the connecting structures between the cartridge sleeve connecting portion 21 at the front end of the housing 20 and the connection portion 12 at the rear end of the cartridge sleeve 1 is an engagement structure. Wherein, multiple engaging protrusions 15 are formed on an outer peripheral surface of the connection portion 12 at the rear end of the cartridge sleeve 1. Multiple L-shaped engaging grooves 211 are formed in an inner peripheral wall of the cartridge sleeve connecting portion 21 at the front end of the housing 20. Each L-shaped engaging groove 211 includes a straight groove section being parallel to the central axis A and a transverse section connected to a rear end of the straight groove section. To place the connection portion 12 at the rear end of the cartridge sleeve 1 into the cartridge sleeve connecting portion 21 at the front end of the housing 20, each engaging protrusion 15 slides along the straight groove section of the L-shaped engaging groove 211, then the cartridge sleeve 1 is turned in an angle to move the engaging protrusion 15 to fix and engage with an end of the transverse section of the L-shaped engaging groove 211, hereby locking the cartridge sleeve 1 to the front end of the housing 20.

As shown in FIG. 1, the syringe may further comprise a protection cap 4. The protection cap 4 is able to be sleeved on and surround the cartridge sleeve 1 assembled with the medicine vial 3 and the needle component 3A to protect the medicine vial 3 assembled with the needle component. In addition, a needle cap 3B may be sleeved on the needle component 3A to prevent the needle from being exposed and to ensure safety of use.

Regarding the condition of use of the syringe of the present invention, take the preferable embodiment of the syringe shown in FIGS. 1 and 2 as an example. With reference to FIGS. 13, 14 and FIGS. 6 to 8, and FIG. 12, after the medicine vial 3 filled up with the medicament liquid is installed in the cartridge sleeve 1, the connection portion 12 at the rear end of the cartridge sleeve 1 is placed into the cartridge sleeve connecting portion 21 at the front end of the housing 20 of the injection mechanism 2 for assembly and is limited in position via the positioning flange 13 of the cartridge sleeve 1 abutting against the front end of the housing 20. At the same time, the diagonal tension knob 80 is pushed by the rear end of the cartridge sleeve 1 and moves backward. The non-return ratchet buckles 62 of the metering guide sleeve 60 are abutted by the conical surface 82 of the diagonal tension knob 80 to radially expand to engage with the one-way ratchet portion 23 of the housing 20. Whereby the injection mechanism is in the injection mode, and the syringe is in a dose metering mode.

As shown in FIGS. 15, 16 and 6 to 8, when the needle component 3A is installed at the front end of the cartridge sleeve 1, the medicine injection for a human body is able to be performed. Wherein, the output button 50 at the rear end of the spiral pushing assembly 2A is pushed by the user and the clutch sleeve 40 is pushed by the output button 50 and moves forwardly. When the flexible locking claws 42 at the front end of the clutch sleeve 40 are pushed by the guiding curved surface 32 at the front end of the driving spiral tube 30, the flexible locking claws 42 contract to clamp the metering guide sleeve 60. Whereby the driving spiral tube 30, the clutch sleeve 40, and the metering guide sleeve 60 can be rotated forwardly together. Wherein, because of the threading connection between the driving spiral guiding groove 33 at an external peripheral surface of the driving spiral tube 30 and the spiral guiding rib 25 at an inner peripheral surface of the housing 20, when the driving spiral tube 30 spirally moves forward inside the housing 20, the number of revolutions of the driving spiral tube 30 is equal to the number of revolutions of the total volume control nut 70, around the metering guide sleeve 60, driven by the clutch sleeve 40. The metering guide sleeve 60 is pushed by the diagonal tension knob 80, so the non-return ratchet buckles 62 of the metering guide sleeve 60 expand to engage with the one-way ratchet portion 23 of the housing 20. The metering guide sleeve 60 can only rotate at the fixing point inside the housing 20 and drive the metering screw 90 to linearly move forward to push the piston 3C in the medicine vial 3 to output a predetermined dose of the medicament liquid.

As shown in FIGS. 17, 18 and 6 to 8, after the output of the predetermined dose of the medicament liquid is completed once, the user releases the output button 50 at the rear end of the spiral pushing assembly 2A. The flexible locking claws 42 at the front end of the clutch sleeve 40 are guided by the guiding curved surface 32 at the front end of the driving spiral tube 30, the clutch sleeve 40 moves backwardly and the flexible locking claws 42 expand to release the metering guide sleeve 60. Accordingly, the spiral pushing assembly 2A is able to be pulled backwardly to perform next injection of predetermined dose of the medicament liquid.

As shown in FIGS. 19 to 21 and 6 to 8, after used for multiple times, the medicament liquid in the medicine vial 3 is used up, and the user detaches the cartridge sleeve 1 and the medicine vial 3 therein from the front end of the housing 20. At this time, the force from the cartridge sleeve 1 and subjected to the diagonal tension knob 80 is removed. The diagonal tension knob 80 is subjected to a restoring elastic force from the contraction of the non-return ratchet buckles 62 of the metering guide sleeve 60 and is pushed forward to a default position. Because the non-return ratchet buckles 62 disengage from the one-way ratchet portion 23 of the housing 20, the unidirectional restriction of the metering guide sleeve 60 is released to convert into the standby mode. At this time, the axial guiding groove 94 is aligned with the guiding block 221 in the guiding ring 22 of the housing 20. The metering screw 90 extending out from the housing 20 is pushed back to the default position along the central axis A. The metering guide sleeve 60 rotates backwardly to push the total volume control nut 70 back to an initial full position of the metering guide sleeve 60 along the central axis A. Accordingly, the syringe can be reused.

The above are only the preferred embodiments of the present invention and do not limit the present invention in any form. Although the present invention has been disclosed as above in the preferred embodiments, it is not intended to limit the present invention. Anyone familiar with the professional technology, without departing from the scope of the technical solution of the present invention, can make use of the technical content disclosed above to make slight changes or modification into equivalent embodiments with equivalent changes, but any content that does not depart from the technical solution of the present invention is based on the present invention. Any simple modifications, equivalent changes and modifications made to the above embodiments by technical essence still fall within the scope of the technical solutions of the present invention.

What is claimed is:

1. A syringe detachably assembled with a medicine vial containing medicament liquid and a needle component connected to a front end of the medicine vial, characterized in that, the syringe defines a central axis extending along a front-to-back direction of the syringe; the syringe comprises an injection mechanism; the injection mechanism has an injection mode and a standby mode, and is able to be manually triggered to perform a conversion between the injection mode and the standby mode; the injection mechanism comprises:

- a housing having a movable space formed through the housing along the central axis, a front end of the housing detachably connected to the medicine vial; and a one-way ratchet portion formed on a peripheral wall of the movable space at a front segment of the movable space of the housing;
- a spiral pushing assembly mounted in the movable space of the housing and being capable of spirally moving around the central axis; the spiral pushing assembly extending to an outside of a rear end of the housing; and the spiral pushing assembly being able to be pushed to generate a spiral propulsion;
- a metering guide sleeve mounted in the housing, being capable of rotating at a fixing point; and the metering guide sleeve inserted into the spiral pushing assembly and able to be controlled to connect and rotate with the spiral pushing assembly; the metering guide sleeve comprising a guide sleeve body and multiple non-return ratchet buckles; the guide sleeve body having a guide sleeve central hole, at least one spiral portion formed on an inner peripheral wall of the guide sleeve central hole; a guide sleeve threaded portion formed on a rear segment of an outer peripheral surface of the guide sleeve body; and a guide sleeve front end portion formed at a front end of the guide sleeve body; the multiple non-return ratchet buckles formed on an external surface of the guide sleeve front end portion; when the multiple non-return ratchet buckles controlled to engage with the one-way ratchet portion of the housing, the metering guide sleeve solely driven to rotate forwardly and in said injection mode; when the multiple non-return ratchet buckles disengaging from the one-way ratchet portion of the housing, the metering guide sleeve able to rotate forwardly or backwardly and in said standby mode;

a total volume control nut mounted in the spiral pushing assembly, being capable of linearly moving along the central axis, and screwed with the guide sleeve threaded portion at a rear segment of the metering guide sleeve;

a diagonal tension knob mounted in the front end of the housing and being movable along the central axis; the diagonal tension knob being drivable to change an engaging condition of the non-return ratchet buckles relative to the one-way ratchet portion of the housing and to convert the said injection mode and the said standby mode; and a metering screw inserted in the diagonal tension knob and the housing and the metering screw screwed within the metering guide sleeve; the metering screw having a screw body having a screw threaded portion and the metering screw screwed with said at least one spiral portion inside the metering guide sleeve via the screw threaded portion; a front end of the metering screw extending in front of the diagonal tension knob; a spiral movement of the metering guide sleeve able to drive the metering screw to move linearly along the central axis inside the housing to perform a quantitative output of the medicament liquid in the medicine vial; when the injection mechanism in the standby mode, the metering screw being able to linearly move backward and be received into the housing along the central axis.

2. The syringe as claimed in claim 1, characterized in that, the syringe comprises a cartridge sleeve; the cartridge sleeve has a containing space formed through and within the cartridge sleeve along the central axis; the cartridge sleeve is detachably installed to the medicine vial, and a front end of the cartridge sleeve is detachably installed to the needle component; the cartridge sleeve is able to be connected to the front end of the housing of the injection mechanism; and the cartridge sleeve is able to trigger the diagonal tension knob to move backward and to drive the multiple non-return ratchet buckles to engage with the one-way ratchet portion of the housing and in the said injection mode; and when the cartridge sleeve is detached from the front end of the housing of the injection mechanism, the diagonal tension knob is able to move forward to make the multiple non-return ratchet buckles disengage from the one-way ratchet portion of the housing and in the said standby mode.

3. The syringe as claimed in claim 2, characterized in that, the cartridge sleeve comprises a cartridge body; the cartridge body has at least one viewing window formed in a peripheral wall of the cartridge body; a connection portion is formed at a rear end of the cartridge body; a positioning flange is formed on the peripheral wall of the cartridge body and located at a front end of the connection portion; multiple engaging protrusions are formed on an outer peripheral surface of the connection portion; the front end of the housing is a cartridge sleeve connecting portion; multiple L-shaped engaging grooves are formed in an inner peripheral wall of the cartridge sleeve connecting portion, each L-shaped engaging groove includes a straight groove section being parallel to the central axis and a transverse section connected to a rear end of the straight groove section; when the connection portion at the rear end of the cartridge sleeve is inserted into the cartridge sleeve connecting portion at the front end of the housing, each engaging protrusion is able to slide along the straight groove section of a respective one of the L-shaped engaging grooves and to turn into an end of the transverse section of the respective one of the L-shaped engaging grooves to lock the cartridge sleeve to the front end of the housing.

4. The syringe as claimed in claim 1, characterized in that, a guiding ring is formed in the front end of the housing; an outer peripheral surface of the guiding ring is connected to the peripheral wall of the movable space via multiple arms; a spacing is formed between the guiding ring and the peripheral wall of the movable space; at least one guiding block is formed on an inner annular wall of the guiding ring; the screw body of the metering screw has at least one axial guiding groove passing through the screw threaded portion and being parallel to the central axis; said at least one axial guiding groove engages with said at least one guiding block inside the guiding ring of the housing.

5. The syringe as claimed in claim 4, characterized in that, each non-return ratchet buckle has a wing protruding forwardly and disposed at a front end face of the non-return ratchet buckle; the diagonal tension knob has a conical surface abutting against the wing of each non-return ratchet buckle to let the conical surface of the diagonal tension knob push the non-return ratchet buckle to engage with the one-way ratchet portion of the housing via the wing.

6. The syringe as claimed in claim 5, characterized in that, the syringe comprises a cartridge sleeve; the cartridge sleeve has a containing space formed through and within the cartridge sleeve along the central axis; the cartridge sleeve is detachably installed to the medicine vial, and a front end of the cartridge sleeve is detachably installed to the needle component; the cartridge sleeve is able to be connected to the front end of the housing of the injection mechanism; and the cartridge sleeve is able to trigger the diagonal tension knob to move backward and to drive the multiple non-return ratchet buckles to engage with the one-way ratchet portion of the housing and in the said injection mode; and when the cartridge sleeve is detached from the front end of the housing of the injection mechanism, the diagonal tension knob is able to move forward to make the multiple non-return ratchet buckles disengage from the one-way ratchet portion of the housing and in the said standby mode.

7. The syringe as claimed in claim 6, characterized in that, the cartridge sleeve comprises a cartridge body; the cartridge body has at least one viewing window formed in a peripheral wall of the cartridge body; a connection portion is formed at a rear end of the cartridge body; a positioning flange is formed on the peripheral wall of the cartridge body and located at a front end of the connection portion; multiple engaging protrusions are formed on an outer peripheral surface of the connection portion; the front end of the housing is a cartridge sleeve connecting portion; multiple L-shaped engaging grooves are formed in an inner peripheral wall of the cartridge sleeve connecting portion, each L-shaped engaging groove includes a straight groove section being parallel to the central axis and a transverse section connected to a rear end of the straight groove section; when the connection portion at the rear end of the cartridge sleeve is inserted into the cartridge sleeve connecting portion at the front end of the housing, each engaging protrusion is able to slide along the straight groove section of a respective one of the L-shaped engaging grooves and to turn into an end of the transverse section of the respective one of the L-shaped engaging grooves to lock the cartridge sleeve to the front end of the housing.

8. The syringe as claimed in claim 1, characterized in that, the housing has at least one spiral guiding rib formed on an inner peripheral wall of the housing; the spiral pushing assembly comprises a driving spiral tube, a clutch sleeve, and an output button, wherein:

the driving spiral tube is mounted in and is capable of spirally moving in the movable space of the housing; the driving spiral tube has a spiral tube channel formed through the driving spiral tube along the central axis, a guiding curved surface formed at a front segment of the spiral tube channel and converging forwardly along the central axis, a driving spiral guiding groove formed in an external peripheral wall of the driving spiral tube and screwed with the at least one spiral guiding rib of the housing, and a spiral tube rear end portion disposed at a rear end of the driving spiral tube; the spiral tube rear end portion extends to an outside of the rear end of the housing and is blocked by the rear end of the housing;

the clutch sleeve is mounted in the spiral tube channel of the driving spiral tube and is able to move linearly relative to the driving spiral tube; the clutch sleeve has a sleeve body, multiple flexible locking claws formed at a front end of the sleeve body, and a connecting end portion disposed at a rear end of the sleeve body; a sleeve channel is formed in the sleeve body and extends along the central axis; at least one sleeve guide groove portion is formed on a peripheral wall of the sleeve channel and is parallel to the central axis; the multiple flexible locking claws have flexibility for radial expansion and contraction; when the clutch sleeve is moved frontward relative to the driving spiral tube, the multiple flexible locking claws are abutted by the guiding curved surface at a front end of the driving spiral tube and contract radially; and the multiple flexible locking claws are capable of bouncing backward to an original position along the guiding curved surface and expand;

the output button is disposed at an outside behind the rear end of the housing and is connected with the connecting end portion at a rear end of the clutch sleeve;

the metering guide sleeve is inserted in the driving spiral tube and the clutch sleeve and is able to be clamped by the multiple flexible locking claws of the clutch sleeve;

the total volume control nut has at least one flange rib formed on an outer peripheral surface of the total volume control nut and engaging with said at least one sleeve guide groove portion of the clutch sleeve.

9. The syringe as claimed in claim 8, characterized in that, each of the flexible locking claws has a locking surface formed at an inner surface of the flexible locking claw; the locking surface of each of the flexible locking claws has multiple straight stripes extending along a front-to-back direction; the metering guide sleeve has an engaging surface formed on the outer peripheral surface, located between the guide sleeve front end portion and the guide sleeve threaded portion, of the guide sleeve body; the engaging surface has multiple straight stripes being parallel to the central axis and corresponding to the straight stripes of the locking surfaces of the flexible locking claws for engagement.

10. The syringe as claimed in claim 8, characterized in that, the housing has a scale observing window formed at a rear section of an external peripheral wall of the housing; the driving spiral tube has a spiral scale portion formed on the external peripheral wall of the driving spiral tube and being parallel to the driving spiral guiding groove; the spiral scale portion has multiple scale lines able to be observed through the scale observing window of the housing.

11. The syringe as claimed in claim 2, characterized in that, the housing has at least one spiral guiding rib formed on an inner peripheral wall of the housing; the spiral pushing assembly comprises a driving spiral tube, a clutch sleeve, and an output button, wherein:

the driving spiral tube is mounted in and is capable of spirally moving in the movable space of the housing; the driving spiral tube has a spiral tube channel formed through the driving spiral tube along the central axis, a guiding curved surface formed at a front segment of the spiral tube channel and converging forwardly along the central axis, a driving spiral guiding groove formed in an external peripheral wall of the driving spiral tube and screwed with the at least one spiral guiding rib of the housing, and a spiral tube rear end portion disposed at a rear end of the driving spiral tube; the spiral tube rear end portion extends to an outside of the rear end of the housing and is blocked by the rear end of the housing;

the clutch sleeve is mounted in the spiral tube channel of the driving spiral tube and is able to move linearly relative to the driving spiral tube; the clutch sleeve has a sleeve body, multiple flexible locking claws formed at a front end of the sleeve body, and a connecting end portion disposed at a rear end of the sleeve body; a sleeve channel is formed in the sleeve body and extends along the central axis; at least one sleeve guide groove portion is formed on a peripheral wall of the sleeve channel and is parallel to the central axis; the multiple flexible locking claws have flexibility for radial expansion and contraction; when the clutch sleeve is moved frontward relative to the driving spiral tube, the multiple flexible locking claws are abutted by the guiding curved surface at a front end of the driving spiral tube and contract radially; and the multiple flexible locking claws are capable of bouncing backward to an original position along the guiding curved surface and expand;

the output button is disposed at an outside behind the rear end of the housing and is connected with the connecting end portion at a rear end of the clutch sleeve;

the metering guide sleeve is inserted in the driving spiral tube and the clutch sleeve and is able to be clamped by the multiple flexible locking claws of the clutch sleeve;

the total volume control nut has at least one flange rib formed on an outer peripheral surface of the total volume control nut and engaging with said at least one sleeve guide groove portion of the clutch sleeve.

12. The syringe as claimed in claim 3, characterized in that, the housing has at least one spiral guiding rib formed on an inner peripheral wall of the housing; the spiral pushing assembly comprises a driving spiral tube, a clutch sleeve, and an output button, wherein:

the driving spiral tube is mounted in and is capable of spirally moving in the movable space of the housing; the driving spiral tube has a spiral tube channel formed through the driving spiral tube along the central axis, a guiding curved surface formed at a front segment of the spiral tube channel and converging forwardly along the central axis, a driving spiral guiding groove formed in an external peripheral wall of the driving spiral tube and screwed with the at least one spiral guiding rib of the housing, and a spiral tube rear end portion disposed at a rear end of the driving spiral tube; the spiral tube rear end portion extends to an outside of the rear end of the housing and is blocked by the rear end of the housing;

the clutch sleeve is mounted in the spiral tube channel of the driving spiral tube and is able to move linearly relative to the driving spiral tube; the clutch sleeve has a sleeve body, multiple flexible locking claws formed at a front end of the sleeve body, and a connecting end portion disposed at a rear end of the sleeve body; a sleeve channel is formed in the sleeve body and extends along the central axis; at least one sleeve guide groove portion is formed on a peripheral wall of the sleeve channel and is parallel to the central axis; the multiple flexible locking claws have flexibility for radial expansion and contraction; when the clutch sleeve is moved frontward relative to the driving spiral tube, the multiple flexible locking claws are abutted by the guiding curved surface at a front end of the driving spiral tube and contract radially; and the multiple flexible locking claws are capable of bouncing backward to an original position along the guiding curved surface and expand;

the output button is disposed at an outside behind the rear end of the housing and is connected with the connecting end portion at a rear end of the clutch sleeve;

the metering guide sleeve is inserted in the driving spiral tube and the clutch sleeve and is able to be clamped by the multiple flexible locking claws of the clutch sleeve;

the total volume control nut has at least one flange rib formed on an outer peripheral surface of the total volume control nut and engaging with said at least one sleeve guide groove portion of the clutch sleeve.

13. The syringe as claimed in claim 4, characterized in that, the housing has at least one spiral guiding rib formed on an inner peripheral wall of the housing; the spiral pushing assembly comprises a driving spiral tube, a clutch sleeve, and an output button, wherein:

the driving spiral tube is mounted in and is capable of spirally moving in the movable space of the housing; the driving spiral tube has a spiral tube channel formed through the driving spiral tube along the central axis, a guiding curved surface formed at a front segment of the spiral tube channel and converging forwardly along the central axis, a driving spiral guiding groove formed in an external peripheral wall of the driving spiral tube and screwed with the at least one spiral guiding rib of the housing, and a spiral tube rear end portion disposed at a rear end of the driving spiral tube; the spiral tube rear end portion extends to an outside of the rear end of the housing and is blocked by the rear end of the housing;

the clutch sleeve is mounted in the spiral tube channel of the driving spiral tube and is able to move linearly relative to the driving spiral tube; the clutch sleeve has a sleeve body, multiple flexible locking claws formed at a front end of the sleeve body, and a connecting end portion disposed at a rear end of the sleeve body; a sleeve channel is formed in the sleeve body and extends along the central axis; at least one sleeve guide groove portion is formed on a peripheral wall of the sleeve channel and is parallel to the central axis; the multiple flexible locking claws have flexibility for radial expansion and contraction; when the clutch sleeve is moved frontward relative to the driving spiral tube, the multiple flexible locking claws are abutted by the guiding curved surface at a front end of the driving spiral tube and contract radially; and the multiple flexible locking claws are capable of bouncing backward to an original position along the guiding curved surface and expand;

the output button is disposed at an outside behind the rear end of the housing and is connected with the connecting end portion at a rear end of the clutch sleeve;

the metering guide sleeve is inserted in the driving spiral tube and the clutch sleeve and is able to be clamped by the multiple flexible locking claws of the clutch sleeve;

the total volume control nut has at least one flange rib formed on an outer peripheral surface of the total volume control nut and engaging with said at least one sleeve guide groove portion of the clutch sleeve.

14. The syringe as claimed in claim 5, characterized in that, the housing has at least one spiral guiding rib formed on an inner peripheral wall of the housing; the spiral pushing assembly comprises a driving spiral tube, a clutch sleeve, and an output button, wherein:

the driving spiral tube is mounted in and is capable of spirally moving in the movable space of the housing; the driving spiral tube has a spiral tube channel formed through the driving spiral tube along the central axis, a guiding curved surface formed at a front segment of the spiral tube channel and converging forwardly along the central axis, a driving spiral guiding groove formed in an external peripheral wall of the driving spiral tube and screwed with the at least one spiral guiding rib of the housing, and a spiral tube rear end portion disposed at a rear end of the driving spiral tube; the spiral tube rear end portion extends to an outside of the rear end of the housing and is blocked by the rear end of the housing;

the clutch sleeve is mounted in the spiral tube channel of the driving spiral tube and is able to move linearly relative to the driving spiral tube; the clutch sleeve has a sleeve body, multiple flexible locking claws formed at a front end of the sleeve body, and a connecting end portion disposed at a rear end of the sleeve body; a sleeve channel is formed in the sleeve body and extends along the central axis; at least one sleeve guide groove portion is formed on a peripheral wall of the sleeve channel and is parallel to the central axis; the multiple flexible locking claws have flexibility for radial expansion and contraction; when the clutch sleeve is moved frontward relative to the driving spiral tube, the multiple flexible locking claws are abutted by the guiding curved surface at a front end of the driving spiral tube and contract radially; and the multiple flexible locking claws are capable of bouncing backward to an original position along the guiding curved surface and expand;

the output button is disposed at an outside behind the rear end of the housing and is connected with the connecting end portion at a rear end of the clutch sleeve;

the metering guide sleeve is inserted in the driving spiral tube and the clutch sleeve and is able to be clamped by the multiple flexible locking claws of the clutch sleeve;

the total volume control nut has at least one flange rib formed on an outer peripheral surface of the total volume control nut and engaging with said at least one sleeve guide groove portion of the clutch sleeve.

15. The syringe as claimed in claim 6, characterized in that, the housing has at least one spiral guiding rib formed on an inner peripheral wall of the housing; the spiral pushing assembly comprises a driving spiral tube, a clutch sleeve, and an output button, wherein:

the driving spiral tube is mounted in and is capable of spirally moving in the movable space of the housing; the driving spiral tube has a spiral tube channel formed through the driving spiral tube along the central axis, a guiding curved surface formed at a front segment of the spiral tube channel and converging forwardly along the central axis, a driving spiral guiding groove formed in an external peripheral wall of the driving spiral tube and screwed with the at least one spiral guiding rib of the housing, and a spiral tube rear end portion disposed at a rear end of the driving spiral tube; the spiral tube rear end portion extends to an outside of the rear end of the housing and is blocked by the rear end of the housing;

the clutch sleeve is mounted in the spiral tube channel of the driving spiral tube and is able to move linearly relative to the driving spiral tube; the clutch sleeve has a sleeve body, multiple flexible locking claws formed at a front end of the sleeve body, and a connecting end portion disposed at a rear end of the sleeve body; a sleeve channel is formed in the sleeve body and extends along the central axis; at least one sleeve guide groove portion is formed on a peripheral wall of the sleeve channel and is parallel to the central axis; the multiple flexible locking claws have flexibility for radial expansion and contraction; when the clutch sleeve is moved frontward relative to the driving spiral tube, the multiple flexible locking claws are abutted by the guiding curved surface at a front end of the driving spiral tube and contract radially; and the multiple flexible locking claws are capable of bouncing backward to an original position along the guiding curved surface and expand;

the output button is disposed at an outside behind the rear end of the housing and is connected with the connecting end portion at a rear end of the clutch sleeve;

the metering guide sleeve is inserted in the driving spiral tube and the clutch sleeve and is able to be clamped by the multiple flexible locking claws of the clutch sleeve;

the total volume control nut has at least one flange rib formed on an outer peripheral surface of the total volume control nut and engaging with said at least one sleeve guide groove portion of the clutch sleeve.

16. The syringe as claimed in claim 11, characterized in that, each of the flexible locking claws has a locking surface formed at an inner surface of the flexible locking claw; the locking surface of each of the flexible locking claws has multiple straight stripes extending along a front-to-back direction; the metering guide sleeve has an engaging surface formed on the outer peripheral surface, located between the guide sleeve front end portion and the guide sleeve threaded portion, of the guide sleeve body; the engaging surface has multiple straight stripes being parallel to the central axis and corresponding to the straight stripes of the locking surfaces of the flexible locking claws for engagement.

17. The syringe as claimed in claim 13, characterized in that, each of the flexible locking claws has a locking surface formed at an inner surface of the flexible locking claw; the locking surface of each of the flexible locking claws has multiple straight stripes extending along a front-to-back direction; the metering guide sleeve has an engaging surface formed on the outer peripheral surface, located between the guide sleeve front end portion and the guide sleeve threaded portion, of the guide sleeve body; the engaging surface has multiple straight stripes being parallel to the central axis and corresponding to the straight stripes of the locking surfaces of the flexible locking claws for engagement.

18. The syringe as claimed in claim 14, characterized in that, each of the flexible locking claws has a locking surface formed at an inner surface of the flexible locking claw; the locking surface of each of the flexible locking claws has multiple straight stripes extending along a front-to-back direction; the metering guide sleeve has an engaging surface formed on the outer peripheral surface, located between the guide sleeve front end portion and the guide sleeve threaded portion, of the guide sleeve body; the engaging surface has multiple straight stripes being parallel to the central axis and corresponding to the straight stripes of the locking surfaces of the flexible locking claws for engagement.

19. The syringe as claimed in claim 11, characterized in that, the housing has a scale observing window formed at a rear section of an external peripheral wall of the housing; the driving spiral tube has a spiral scale portion formed on the external peripheral wall of the driving spiral tube and being parallel to the driving spiral guiding groove; the spiral scale portion has multiple scale lines able to be observed through the scale observing window of the housing.

20. The syringe as claimed in claim 13, characterized in that, the housing has a scale observing window formed at a rear section of an external peripheral wall of the housing; the driving spiral tube has a spiral scale portion formed on the external peripheral wall of the driving spiral tube and being parallel to the driving spiral guiding groove; the spiral scale portion has multiple scale lines able to be observed through the scale observing window of the housing.

* * * * *